(12) United States Patent
Avey et al.

(10) Patent No.: US 8,032,389 B2
(45) Date of Patent: Oct. 4, 2011

(54) METHOD FOR USE OF ENVIRONMENTAL CLASSIFICATION IN PRODUCT SELECTION

(75) Inventors: Donald P. Avey, Ankeny, IA (US);
Phillip Lee Bax, Johnston, IA (US);
Richard Glenn Brooke, Johnston, IA (US); David S. Ertl, Waukee, IA (US);
Joseph K. Gogerty, Algona, IA (US);
David J. Harwood, Johnston, IA (US);
Michael J. Lauer, Des Moines, IA (US);
Terry Eu Claire Meyer, Urbandale, IA (US); Todd A. Peterson, Johnston, IA (US); Robert C. Iwig, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 427 days.

(21) Appl. No.: 11/423,642

(22) Filed: Jun. 12, 2006

(65) Prior Publication Data

US 2006/0282299 A1 Dec. 14, 2006

Related U.S. Application Data

(60) Provisional application No. 60/689,716, filed on Jun. 10, 2005.

(51) Int. Cl.
*G06Q 99/00* (2006.01)
(52) U.S. Cl. .................................................. 705/1.1
(58) Field of Classification Search ............... 705/1, 1.1
See application file for complete search history.

(56) References Cited

U.S. PATENT DOCUMENTS

| 2,446,509 | A | 8/1948 | Fischer |
| 3,727,345 | A | 4/1973 | Smith |
| 4,159,596 | A | 7/1979 | Downing |
| 4,291,082 | A | 9/1981 | Stall |
| 4,554,761 | A | 11/1985 | Tell |
| 5,492,547 | A | 2/1996 | Johnson |
| 5,538,880 | A | 7/1996 | Lundquist et al. |
| 5,689,914 | A | 11/1997 | Greaves et al. |
| 5,884,244 | A | 3/1999 | Phaal |
| 5,897,619 | A | 4/1999 | Hargrove et al. |
| 5,978,723 | A | 11/1999 | Hale et al. |
| 5,981,832 | A | 11/1999 | Johnson |
| 6,008,756 | A | 12/1999 | Boerhave et al. |
| 6,141,904 | A | 11/2000 | Greaves et al. |

(Continued)

FOREIGN PATENT DOCUMENTS

WO WO 97/09696 A1 3/1997

(Continued)

OTHER PUBLICATIONS

PCT/US 06/22917, Pioneer Hi-Bred International, Inc., International Search Report, Jun. 12, 2006, 3 pages.

(Continued)

*Primary Examiner* — Jonathan Ouellette
(74) *Attorney, Agent, or Firm* — Woodcock Washburn LLP

(57) ABSTRACT

Methods and software for selecting seed products or other agricultural inputs for planting within an associated land base include classifying the land base with an environmental classification, determining at least one seed product to plant within the land base based on the environmental classification, and providing an output comprising identification of the at least one seed product to plant within the land base.

58 Claims, 28 Drawing Sheets

U.S. PATENT DOCUMENTS

| | | | |
|---|---|---|---|
| 6,212,824 | B1 | 4/2001 | Orr et al. |
| 6,282,835 | B1 | 9/2001 | Richtsmeier |
| 6,338,040 | B1 | 1/2002 | Buman et al. |
| 6,433,146 | B1 | 8/2002 | Cheryan |
| 6,455,758 | B1 | 9/2002 | Johnson |
| 6,505,146 | B1 | 1/2003 | Blackmer |
| 6,549,852 | B2 | 4/2003 | Hanson |
| 6,691,135 | B2 | 2/2004 | Pickett et al. |
| 6,778,872 | B2 | 8/2004 | Jorgenson et al. |
| 6,865,556 | B2 | 3/2005 | Penner et al. |
| 6,945,459 | B2 | 9/2005 | Flanagan |
| 6,990,459 | B2 | 1/2006 | Schneider |
| 6,999,877 | B1 | 2/2006 | Dyer et al. |
| 7,039,592 | B1 | 5/2006 | Yegge et al. |
| 7,167,797 | B2 | 1/2007 | Faivre et al. |
| 7,184,892 | B1 | 2/2007 | Dyer et al. |
| 7,193,128 | B2 | 3/2007 | Copenhaver et al. |
| 7,321,310 | B2 | 1/2008 | Curkendall et al. |
| 7,844,475 | B1 | 11/2010 | Murphy |
| 2002/0103688 | A1 | 8/2002 | Schneider |
| 2002/0173980 | A1 | 11/2002 | Daggett et al. |
| 2003/0083819 | A1 | 5/2003 | Rooney et al. |
| 2003/0125877 | A1 | 7/2003 | Hanson |
| 2003/0126635 | A1 | 7/2003 | Penner |
| 2003/0129973 | A1 | 7/2003 | Oishi et al. |
| 2003/0236724 | A1 | 12/2003 | Baranova et al. |
| 2004/0073556 | A1 | 4/2004 | Wood et al. |
| 2004/0132370 | A1 | 7/2004 | Schroder |
| 2004/0133347 | A1 | 7/2004 | Britt |
| 2004/0210509 | A1 | 10/2004 | Eder |
| 2004/0215556 | A1 | 10/2004 | Merkley et al. |
| 2004/0264762 | A1 | 12/2004 | Mas |
| 2005/0027572 | A1* | 2/2005 | Goshert .......................... 705/4 |
| 2005/0096849 | A1* | 5/2005 | Sorrells ......................... 702/19 |
| 2005/0125260 | A1 | 6/2005 | Green et al. |
| 2005/0150160 | A1 | 7/2005 | Norgaard et al. |
| 2005/0153687 | A1 | 7/2005 | Niemenmaa et al. |
| 2005/0153987 | A1 | 7/2005 | Niemenmaa et al. |
| 2005/0208925 | A1 | 9/2005 | Panasik et al. |
| 2005/0283314 | A1 | 12/2005 | Hall |
| 2006/0015253 | A1 | 1/2006 | Ochs et al. |
| 2006/0015360 | A1 | 1/2006 | Ochs et al. |
| 2006/0015374 | A1 | 1/2006 | Ochs et al. |
| 2006/0074560 | A1 | 4/2006 | Dyer et al. |
| 2006/0106539 | A1 | 5/2006 | Choate et al. |
| 2006/0282295 | A1 | 12/2006 | McComb et al. |
| 2006/0282467 | A1 | 12/2006 | Peterson et al. |
| 2006/0287896 | A1 | 12/2006 | McComb et al. |
| 2007/0174095 | A1 | 7/2007 | McComb et al. |
| 2008/0040165 | A1 | 2/2008 | Anderson et al. |
| 2010/0306012 | A1 | 12/2010 | Zyskowski et al. |

FOREIGN PATENT DOCUMENTS

| | | |
|---|---|---|
| WO | WO 01/33505 A2 | 5/2001 |

OTHER PUBLICATIONS

Cooper, M. et al., "Integrating tools and generating information for efficient plant breeding: Past, Present and Future", International Symposium on Plant Breeding, Aug. 17-22, 2003.

"Classification of Maize Environments using Crop Simulation and GIS", Pioneer Crop Genetics Research, presented at CIMMYT, Apr. 15-16, 2003.

Loffler, Carlos M., et al., "Characterization of Maize Environments using Crop Simulation and GIS", 4th International Crop Science Congress, Sep. 2004.

Loffler, Carlos M., "Characterization of Maize Environments Using Crop Simulation and GIS", Presented at University of Florida, September 9, 2004.

Loffler, Carlos M., "Classification of Maize Environments using Crop Simulation and Geographic Information Systems", ASTA Annual Corn and Sorghum Research Conference, Dec. 9, 2004.

Loffler, Carlos M., "New Methodologies for Managing Genotype by Environment Interaction", VIII Congreso Nacional de Maiz, Rosario, Argentina, Nov. 16-18, 2005.

Wei, Jun et al., "Impact of Genotype and Environment on Historical Corn Production in the USA". ASA Annual Meeting, Las Vegas, Nevada, Nov. 2003.

Author Unknown, "Self Pollination Auto Fecondation" Sales page, OSMOLUX: Emerging Technologies—No Contamination, No Rotting, Jun. 18, 2003, 1page.

Author Unknown, "Assessing the Composition of Dairy Products and Grain by Near Infrared," Chemometrics Applications Overview, InfoMetrix, Inc., 1996, 4 pages.

Author Unknown, "Fieldstar Advanced Precision Farming System," AGCO Limited, 2001, 16 pages.

Author Unknown, "Fieldstar-Maximizing Farm Profitability and Improving Environmental Practices," AGCO Corporation, retrieved from website archived Jun. 30, 2004, 2 pages.

Davis, "Corn Milling, Processing and Generation of Co-Products," Minnesota Nutrition Conference, Minnesota Corn Growers Association, Sep. 11, 2001, 7 pages.

Doehlert et al., "Genotyoic and Environmental Effects on Grain Yield and Quality of Oat Grown in North Dakota," Crop Science, Jul.-Aug. 2001, vol. 41, pp. 1066-1072.

Haefele et al., "Selection and Optimization of Corn Hybrids for Fuel Ethanol Production," American Seed Trade Association's Proceedings of the 59$^{th}$Annual Corn and Sorghum Research Conference, Dec. 2004, 21 pages.

Hume, "A Possible New Method for the Control of Pollen in Corn," Journal of the American Society of Agronomy, Mar. 1941, vol. 33, No. 3, pp. 265-266.

Mazur et al., "Gene Discovery and Product Development for Grain Quality Traits," Science, Jul. 16, 1999, vol. 285, pp. 372-374.

Semchenko et al., "The Effect of Breeding on Alometry and Phenotypic Plasticity in Four Varieties of Oat," Field Crops Research, Sep. 14, 2005, vol. 93, Issues 2-3, pp. 151-168, http://www.sciencedirect.com, accessed Jun. 3, 2009.

Thomison, "Cultural Practices for Optimizing Maize Seed Yield and Quality in Production Fields," M.B. McDonald and S. Contreras (ed.) Proceedings International Seed Seminar: Trade, Production and Technology, Oct. 15-16, 2002, pp. 49-55.

Tiffany et al., "Factors Associated with Success of Fuel Ethanol Products," Staff Paper P03-7, Department of Applied Economics, College of Agricultural, Food, and Environmental Sciences, University of Minnesota, Aug. 2003, 62 pages.

Wehling et al., "Prediction of Corn Dry-Milling Quality by Near-Infrared Spectroscopy," Cereal Chemistry, 1996, vol. 73, No. 5, pp. 543-546.

Author Unknown, "Assessing the Composition of Dairy Products and Grain by Near Infrared," Chemometrics Applications Overview, InfoMetrix, Inc., 1996, 4 pages.

International Search Report, Pioneer Hi-Bred International, Inc., PCT/US07/88510, Dec. 21, 2007, 2 pages.

Thomison, "Cultural Practices for Optimizing Maize Seed Yield and Quality in Production Fields," M.B. McDonald and S. Contreras (ed.) Proceedings International Seed Seminar: Trade, Production and Technology, Oct. 15-16, 2002, pp. 49-55.

* cited by examiner

| 152 Recommendations ☒ | | | |
|---|---|---|---|
| 154 Product | 156 Acres | 157 Risk Assessment | 158 Crop Revenue Assurance |
| Hybrid1 | Acres1 | X prob | $1 |
| Hybrid2 | Acres2 | Y prob | $2 |
| Hybrid3 | Acres3 | Z prob | $3 |

Site Specific Information

Location [_____] —172

Environment and Production Information

Maturity Days [▼]
—176
Input Traits [▼]
—178
Output Traits [▼]
—180
Seed Treatment [▼]
—182
Tillage Practice [▼]
—174
Planting Population [_____]
—184
Nitrogen Utilization [▼]
—186
Drought Frequency [_____]
—187
Field Attributes [▼]
—185

[ Select Hybrid ]

| Hybrid Name | Hybrid Rank | Risk Assessment 189 |
|---|---|---|
| Hybrid1 | 99% | 0.075 prob |
| Hybrid2 | 89% | 0.15 prob |

HYBRID PORTFOLIO MANAGER: TABLE MODE

| Field Name | Home |
|---|---|
| Field Size | 32 Acres |
| Field ID | 1234 ▼ |
| Maturity | |
| Trait Needs | White |
| | ECB |
| | CRW |
| | RR |
| | YFC |
| | WAXY |
| | EU Approved |
| Market Neeed | No restriction ▼ |

[Produce EnClass (SM) Driven Hybrid Suggestions]

[Add new Field]

[Go to map based version]

FIG. 24

REPORT MODE: WEIGHTED TRAIT ANALYSIS

| Hybrids | Acres | Stalks | Roots | Dry down | GLS | Anthra cnose | Stay Green | Drought | Test Weight | Coastal Plain |
|---|---|---|---|---|---|---|---|---|---|---|
| HYBRID1 | 100.0 | 3 | 4 | 5 | 4 | 4 | 4 | 4 | 4 | 4 |
| HYBRID2 | 250.0 | 4 | 4 | 4 | 5 | 5 | 4 | 3 | 3 | 3 |
| HYBRID3 | 39.0 | 5 | 4 | 5 | 6 | 3 | 6 | 7 | 8 | 4 |
| HYBRID4 | 200.0 | 3 | 3 | 3 | 3 | 3 | 3 | 3 | 4 | 4 |
| HYBRID5 | 100.0 | 4 | 4 | 4 | 4 | 4 | 4 | 4 | 4 | 4 |
| HYBRID6 | 25.0 | 6 | 5 | 5 | 6 | 6 | 5 | 6 | 6 | 5 |
| HYBRID7 | 50.0 | 4 | 4 | 5 | 5 | 4 | 4 | 4 | 4 | 5 |
| HYBRID8 | 100.0 | 6 | 5 | 3 | 3 | 5 | 5 | 4 | 4 | 4 |
| HYBRID9 | 20.0 | 4 | 4 | 5 | 5 | 4 | 4 | 4 | 4 | 4 |
| HYBRID10 | 100.0 | 4 | 5 | 5 | 5 | 5 | 5 | 5 | 5 | 5 |
| HYBRID11 | 200.0 | 3 | 4 | 4 | 4 | 4 | 4 | 4 | 5 | 3 |
| Total/Weighted Acres | 1184.0 | 3.7 | 3.7 | 4.0 | 4.3 | 4.1 | 3.9 | 3.6 | 3.9 | 3.7 |

Go to Hybrid Mix Manager

FIG. 26

REPORT TOOL: HYBRID MIX MANAGER

Cutomer B

|  |  | Environment Class | | | | Long Term Average |
|---|---|---|---|---|---|---|
|  |  | Temperate | Temperate Humid | Temperate Dry | High Latitude | |
| Frequency |  | 30% | 30% | 20% | 20% | 100% |
| Hybrid W | 5% | 105 | 95 | 100 | 90 | 98 |
| Hybrid X | 70% | 115 | 102 | 105 | 80 | 102.1 |
| Hybrid Y | 5% | 100 | 100 | 95 | 95 | 98 |
| Hybrid Z | 20% | 105 | 105 | 110 | 85 | 102 |
| Average |  | 106.25 | 100.5 | 102.5 | 87.5 | |
|  |  | 111.75 | 102.15 | 105.25 | 82.25 | 101.67 |

Risk profile   Risk tolerant.   Will accept more year to year variability in order to capitalize on high yield conditions.

Invoice Current Product Mix

FIG. 27

INVOICING SYSTEM

Pioneer's Hybrid Portfolio Manager will be sending the following information to Pioneer's invoicing system.

Based on your acreage of: 1184
And the following product mix:

| Hybrids | Acres | Percent of Acres | Units |
|---|---|---|---|
| HYBRID1 | 100.0 | 8.4 | 40 |
| HYBRID2 | 250.0 | 21.1 | 100 |
| HYBRID3 | 39.0 | 3.3 | 16 |
| HYBRID4 | 200.0 | 16.9 | 80 |
| HYBRID5 | 100.0 | 8.4 | 40 |
| HYBRID6 | 25.0 | 2.1 | 10 |
| HYBRID7 | 50.0 | 4.2 | 20 |
| HYBRID8 | 100.0 | 8.4 | 40 |
| HYBRID9 | 20.0 | 1.7 | 8 |
| HYBRID10 | 100.0 | 8.4 | 40 |
| HYBRID11 | 200.0 | 16.9 | 80 |
| Totals | 1184.0 | 100 | 474 |

Start new farm plan

FIG. 28

METHOD FOR USE OF ENVIRONMENTAL CLASSIFICATION IN PRODUCT SELECTION

CROSS-REFERENCE TO RELATED APPLICATIONS

This application claims priority under 35 U.S.C. §119 of a provisional application Ser. No. 60/689,716 filed Jun. 10, 2005, which application is hereby incorporated by reference in its entirety.

BACKGROUND OF THE INVENTION

The present invention provides for computer-implemented methods and related methods to assist a crop producer or other in selecting agricultural inputs, such as seed products to use in one or more fields, or to predict or describe relative performance of one or more seed products.

The problem is generally described in the context where the seed products are corn hybrids. The current industry-wide approach to delivering product performance information for use in hybrid selection by producers is to use numerous comparative yield measurements from recent years (primarily the most recent year) and the geography considered relevant to the producer. Use of recent product performance data in selection of hybrids is not completely indicative of future hybrid performance as environmental and biotic factors vary from year to year, including extreme weather events, such as drought or flooding and pest or disease prevalence. Moreover, this approach does not fully take into account environmental and biotic factors important to a hybrid's performance. Furthermore, this approach lacks the full assessment of the relevance of the information generated by the trials to the relative performance of cultivars (genotype by environment interaction), for example genetic correlations. It assumes recent experience is the best predictor of future relative hybrid performance, regardless of how representative the recent experience may or may not be of the long-term environmental profile of the producer's land base.

In addition, this selection approach does not take into account a producer's objectives for productivity, nor does it allow for objective and specific recommendations of seed products or other crop product considerations, for example, fertilizer types or irrigation needs, for a particular land base so that producers may minimize their risk of unexpected performance occurrences. Although risk is uncertain, it is manageable.

What is needed is a method for product selection that is useful in characterizing relative performance of different seed products so that risk can be managed.

SUMMARY OF THE INVENTION

Therefore it is a primary object, feature, or advantage of the present invention to improve over the state of the art.

Another object, feature, or advantage of the present invention is to provide a method to assist customers, including producers, in managing risks associated with crop production.

Yet another object, feature, or advantage of the present invention is to assist customers and others in understanding relative performance of different agricultural inputs, including seed products, under the same or similar environmental conditions.

A still further object, feature, or advantage of the present invention is to assist customers and others in understanding relative performance of an agricultural input, such as a seed product, under a range of environmental conditions.

Another objective, feature, or advantage of the present invention is to assist producers in selecting the best seed product for a particular location.

It is a further object, feature, or advantage of the present invention to describe genotype-by-environment interactions that may affect performance of a seed product.

It is a still further object, feature, or advantage of the present invention to improve management of risks associated with genotype-by-environment interactions.

It is a further object, feature, or advantage of the present invention to improve product selection decisions.

A further object, feature, or advantage of the present invention is to increase the likelihood of high product performance.

A still further object, feature, or advantage of the present invention is to increase the probability of customer satisfaction in seed products.

A further object, feature, or advantage of the present invention is to increase yield advantage of a product.

Another object, feature, or advantage of the present invention is to assist customers in selection of these products most adapted to their land base.

Yet another object, feature, or advantage of the present invention is to increase sales force confidence in products and positioning of products.

A further object, feature, or advantage of the present invention is to increase customer confidence in products and positioning recommendations.

A still further object, feature, or advantage of the present invention is to provide environmental and product specific risk management tools.

A still further object, feature, or advantage of the present invention is to provide product portfolio analysis and planning.

Another object, feature, or advantage of the present invention is to provide portfolio risk assessment.

Another object, feature, or advantage of the present invention is to use genotype by environment interaction analysis to aid crop performance prediction for strategic farm operation decision making.

A still further object, feature, or advantage of the present invention is to weight genotype by environment data based on long-term frequencies to facilitate a prediction of product performance.

A further object, feature, or advantage of the present invention is to use genotype by environment information to capture more data from a broader area to use for a localized area.

Yet another object, feature, or advantage of the present invention is to increase a producer's confidence in planning recommendations.

A further object, feature, or advantage of the present invention is to minimize risk of unexpected crop performance occurrences.

A still further object, feature, or advantage of the present invention is to aid a producer faced with a novel situation in selecting a hybrid that can adapt to a particular environmental or biotic condition.

Another object, feature, or advantage of the present invention is to identify hybrid performance issues or concerns for a particular land base.

Yet another object, feature, or advantage of the present invention is to minimize crop performance risks by making "sound" business decisions based on complete and accurate environmental, genotype, and biotic data and genotype by environment performance analysis.

Yet another object, feature, or advantage of the present invention is to use genotype by environment interactions to categorize particular land bases into different environmental classifications.

A still further object, feature, or advantage of the present invention is to allow for the creation of an environmental profile for all or part of a particular land base.

A still further object, feature, or advantage of the present invention is to create a portfolio of cultivars that maximize the probability that a producer's objectives for productivity will be met.

Yet another object, feature, or advantage of the present invention is to produce an environmental performance profile of crop cultivars for a particular land base.

It is to be understood that the present invention has a number of different aspects, each of which may demonstrate one or more of these and/or other objects, features, or advantages of the present invention as will become apparent from the specification that follows.

The present invention has numerous aspects that build upon the application of environment classification and information extracted from hybrids. These various aspects are often described herein from the perspective of a seed company and a crop producer and when a specific crop is used as an example, the exemplary crop is usually corn. Of course, aspects of the present invention are applicable to many different types of companies or individuals and many different types of agricultural inputs and/or products. Also, the present invention is of use not just to crop producers but others who have interest in comparing relative performance of agricultural inputs under different conditions. This could include, for example, downstream users of agricultural products, such as processors, livestock producers, agricultural input suppliers such as equipment manufacturers, chemical producers, landlords, or others who have interests related to agricultural production.

The present invention relates to improved understanding of genotype-by-environment interactions and applications of those methods in a variety of contexts for a variety of purposes.

According to one aspect of the invention a computer-assisted method of selecting seed products for planting by a crop producer associated with a land base is provided. Each of the seed products has a genotype. The method includes providing an environmental profile for the land base, determining a recommendation of at least one seed product to plant within the land base based on the environmental profile and performance of the genotype of each of the seed products in the environmental profile of the land base, and providing an output comprising identification of the at least one seed product to plant within the land base. The environmental profile can include an environmental classification associated with the land base. The determination of a recommendation is preferably at least partially based on genotype-by-environment interactions. The environmental profile can include agronomic information, meteorological information, and field experimentation information. In addition a producer profile for the crop producer can be used. The producer profile can include any number of non-environmental preferences including preferred production practices. These may include risk tolerance information, business goals of the producer, productivity goals of the producer, financing information, insurance information, tillage information, size of farm information, number of farms information, landlord preference information, equipment limitations, and work force limitations. The environmental profile may include wind data, temperature data, solar radiation data, precipitation data, soil type data, soil pH data, planting and harvesting dates, irrigation data, tiled area data, previous crop data, fertilizer data, nitrogen level data, phosphorous level data, potassium level data, insecticide data, herbicide data, and biotic data.

According to another aspect of the invention, a computer-assisted method of selecting seed products for planting by a crop producer associated with a land base is provided. The method includes providing a characterization of the land base and associating a risk level with the crop producer. Next the method provides for determining at least one seed product to plant within the land base based on the risk level, the characterization of the land base, and genotype-by-environment interactions associated with the seed products. An output is then provided which identifies at least one seed product to plant within the land base. The characterization of the land base may be based partially on environmental and/or physiological landmark data. The genotype-by-environment interactions may be determined at least partially based on performance data associated with the seed products.

According to another aspect of the present invention, a computer-assisted method of selecting seed products for planting by a crop producer associated with a land base is provided. The method includes classifying the land base with an environmental classification, determining at least one seed product to plant within the land base based on the environmental classification, and providing an output comprising identification of the at least one seed product to plant within the land base.

According to another aspect of the present invention, a computer-assisted method of determining a seed product that is likely to be a high performer for a producer's particular land base is provided. The method includes providing a data bank comprising at least one seed product's prior performance, wherein each seed product's prior performance was determined at different locations under different environmental, biotic or abiotic conditions or a combination of said conditions. The method further includes providing a characterization of a producer's particular land base, selecting and retrieving from the data bank seed products that have been grown in locations the same or similar to the producer's particular land base, comparing the performance data of said products grown in locations similar to the producer's particular land base with one another, determining whether a seed product performed better than other seed products, and providing an output comprising an identification of at least one seed product that is likely to be a high performer for the producer's particular land base.

According to another aspect of the present invention, a computer-assisted method of selecting a portfolio of seed products for planting within a land base associated with a producer is provided. Each of the seed products has a genotype. The method includes dividing the land base into regions, providing an environmental profile for each of the regions of the land base, and determining a recommendation of a plurality of seed products to plant within each region of the land base. The recommendation is partially based on interaction of the genotype of each seed product with the environmental profile, and relative performance of the seed product within the environmental profile across potential variations.

According to another aspect of the present invention, a method of selecting a portfolio of seed products for planting within a land base associated with a producer is provided. Each of the seed products has a genotype. The method includes dividing the land base into regions, accessing an environmental profile for each of the regions of the land base, determining potential variations in the environmental profile during a growing season, and providing a recommendation for the portfolio of seed products to plant within the land base. The recommendation includes a selection of at least one seed product for each region of the land base. The recommendation for the portfolio is based on the environmental profile for each of the regions and potential variations in the environmental profile to thereby manage risks associated with the potential variations.

According to another aspect of the present invention, an article of software adapted for assisting a producer in selecting a mix of seed products to plant within a the producer's fields is provided. The software may include a first screen display adapted for identifying the plurality of fields controlled by the producer and a size of each of the plurality of fields and a second screen display adapted for displaying performance of a plurality of seed products over a range of environment classes. The software may have a reporting mode adapted for reporting which one or more of the plurality of seed products to plant within each of the plurality of fields. The software may further have a means for electronically communicating information regarding the producer's choices of seed products to an invoicing system.

BRIEF DESCRIPTION OF THE FIGURES

FIG. 11 is a screen display showing a product portfolio according to one embodiment of the present invention.

FIG. 12 is a screen display for one embodiment of an application of the present invention.

FIG. 24 provides one embodiment of a screen display in a table mode.

FIG. 26 illustrates another example of a screen display associated with a reporting mode.

FIG. 27 illustrates another embodiment of a screen display according to one embodiment of the present invention.

FIG. 28 provides a screen display according to one embodiment of the present invention which lists selected seed products and information communicated to an invoicing system.

DETAILED DESCRIPTION OF THE PREFERRED EMBODIMENT

Figure 1:
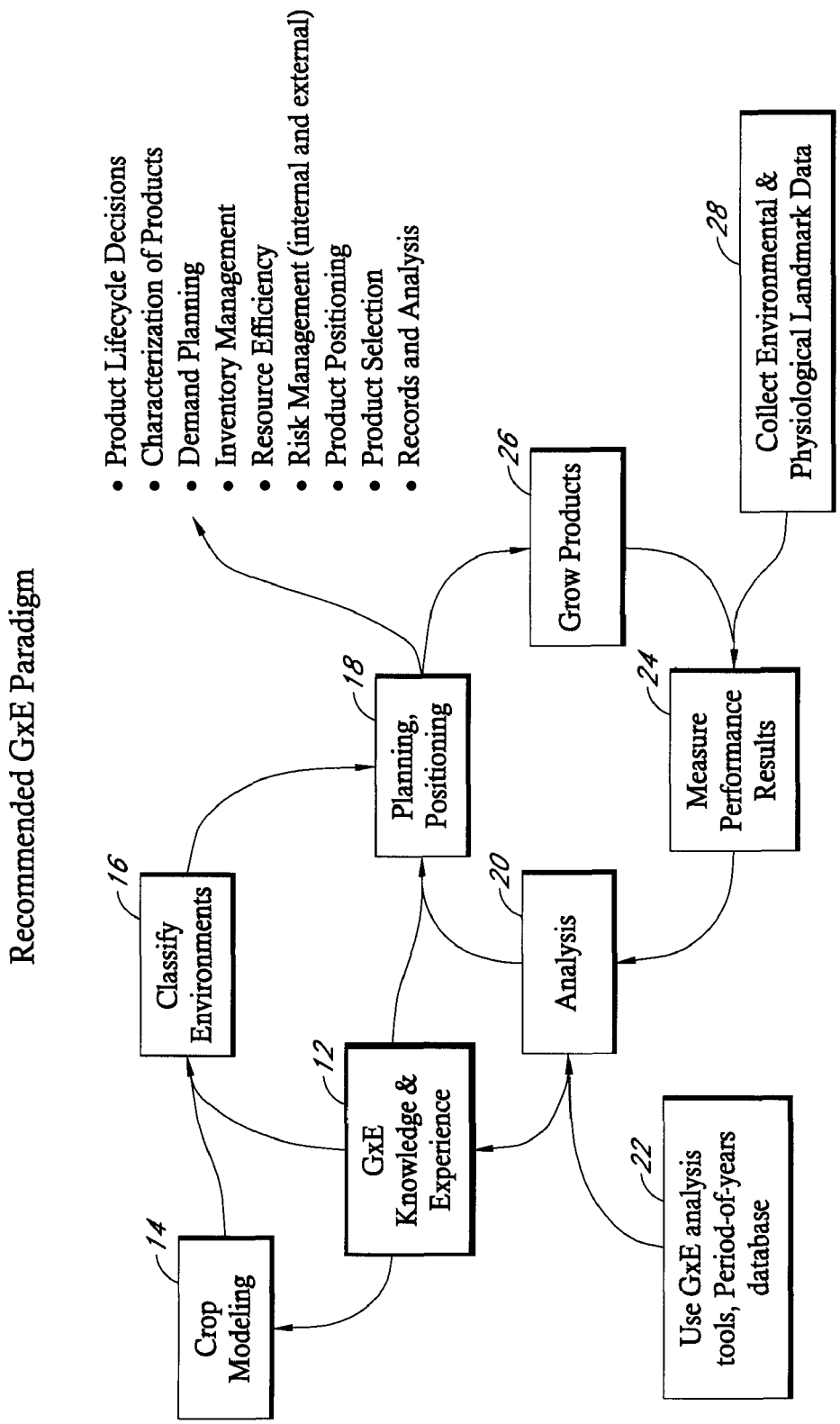
FIG. 1 is a flow diagram illustrating one process for determining genotype-by-environment interactions and using that information in categorizing land bases into different environmental classifications.

The present invention provides methods which can be used to assist customers, including producers or others in managing risks related to crop production. Managing risks can be performed by understanding the relative performance of different agricultural inputs, including seed products, under the same or similar environmental conditions as well as understanding variations in the performance of the same agricultural input over a range of environmental conditions. By being able to describe and understand these variations in performance, decisions can be made which are consistent with overall business and/or production objectives and limit risk associated with variations in environmental conditions. These decisions can include what seed products or combination of seed products to plant, where to plant different seed products, what other agricultural inputs to use, and what crop management practices to apply.

One method to manage risks associated with crop production uses knowledge of genotype-by-environment interactions to assist a producer or other customer in selecting seed products to plant in one or more fields. A "genotype" is generally defined as a cultivar, genetically homogenous (lines, clones), a hybrid of two or more parents, or heterogeneous (open-pollinated populations). An "environment" is generally defined as a set of conditions, such as climatic conditions, soil conditions, biotic factors (such as, without limitation, pests and diseases) and/or other conditions that impact genotype productivity. "Management" as used in this context generally refers to production management decisions, such as, but not limited to crop production practices. In addition, the present invention allows for the use of environmental characterizations to assist in describing genotype-by-environment interactions. It is to be understood that the term "genotype-by-environment" (G×E) is to encompass what is sometimes known or referred to as "genotype-by-environment-by management" (G×E×M) as the environment associated with a plant may include management practices which affect the environment (for example, irrigation may be considered a management practice, but use of irrigation affects the growing environment).

Following, is an exemplary description regarding the use of G×E interactions and environmental classification. Next, an exemplary description is provided regarding how a producer or other customer uses this information in order to make decisions.

G×E and Environmental Classification

Genetic manipulation alone does not ensure that a plant will perform well in a specific environment or for that matter a wide range of environments year after year. In other words, there is no one genotype that is likely to performance best in all environments or under all management practices. The performance or phenotype results from an interaction between the plant's genotype and the environment and the management practices used.

It is to be understood that there are some inherent difficulties in understanding such interactions. An environment at a given location changes over the years making multi-environment trials (METs) performed in the same location limited as to inferences about future crop performance. Furthermore, inferences about a crop's future performance in different locations depend on whether the target population of environments (TPEs) is well sampled since the environment varies between different locations in one year.

To assist in analyzing such interactions, the present invention preferably uses environmental classification techniques. The environmental classification techniques are used, preferably with a large set of data to relate performance of different genotypes to different environments. Environmental classification is then used when selecting the best seed products for a particular land base. Thus, for example, a producer can use environmental classification to select the best seed products for their land base based on the expected environmental conditions. Alternatively, the producer may diversify and select a combination of seed products based on a range of expected environmental conditions to thereby manage risks associated with environmental variability. Of course, environmental classification can be used by not just producers but others having interest in agricultural production.

FIG. 1 provides an overview of one G×E paradigm where G×E knowledge 12 is used in planning and positioning 18. G×E knowledge 12 can be applied to crop modeling 14. Crop modeling 14 and G×E knowledge 12 may either alone or together be used to classify environments. The G×E knowledge 12 and classified environments may be used in facilitating the positioning and/or planning 18 strategies, such as characterization of products, resource efficiency, risk management, product positions, and product selection.

Subsequent to positioning and planning, the producer will grow the selected products 26 and measure the performance results 24. The producer may also collect environmental and physiological landmark data 28 and in conjunction with performance results 24 use it in analysis 20. Analysis of environmental and physiological landmark data 28 and performance results 24 may undergo analysis 20 using G×E analysis tools or period-of-years database 22.

Building an Environmental Classification System

The effectiveness of a product evaluation system for genotype performance largely depends on the genetic correlation between multi-environment trials (MET) and the target population of environments (TPE) (Comstock, R. E. 1977. 'Proceedings of the International Conference on Quantitative Genetics, Aug. 16-21, 1976' pp. 705-18. Iowa State University Press. Ames, USA.). For example, previous characterizations of maize environments relied mainly on climatic and soil data (e.g. Hartkamp, A. D., J. W. White, A. Rodriguez Aguilar, M. Bänziger, G. Srinivasan, G. Granados, and J. Crossa. 2000. Maize Production Environments Revisited: A GIS-based Approach. Mexico, D. F. CIMMYT.; Pollak, L. M., and J. D. Corbett. 1993. Agron. J. 85:1133-1139; Runge, E. C. A. 1968. Agron. J. 60:503-507.). While useful to describe environmental variables affecting crop productivity, these efforts did not quantify the impact of these variables on the genetic correlations among testing sites. Consequently, plant breeders have more extensively used characterizations of environments based on similarity of product discrimination in product evaluation trials (e.g. Cooper, M., D. E. Byth, and I. H. DeLacy. 1993. Field Crops Res. 35:63-74.). However, these efforts frequently fail to provide a long-term assessment of the target population of environments (TPE), mainly due to the cost and impracticality of collecting empirical performance data for widespread and long-term studies.

The present invention provides a modern approach of product evaluation where a TPE is described. The description of a TPE includes classifying the land base into an environmental class and assessing the frequency of occurrence of the range of environments experienced at a given location. The present inventors contemplate that areas of adaption (AOA) could also be evaluated. As used herein AOA refers to a location with the environmental conditions that would be well suited for a crop or specific genotype. Area of adaption is based on a number of factors, including, but not limited to, days to maturity, insect resistance, disease resistance, and drought resistance. Area of adaptability does not indicate that the crop will grow in every location or every growing season within the area of adaption or that it will not grow outside the area. Rather it defines a generally higher probability of success for a crop or genotype within as opposed to outside that area of adaptation.

The environmental information collected may be used to develop an environmental database for research locations. Initially, multiple environment trials are performed by planting different genotypes available from a variety of sources, e.g. germplasm, inbreds, hybrids, varieties in multiple environments. These trials aid the determination of whether the TPEs are homogenous or should be categorized into different environmental classifications. The performance data of these genotypes and environmental and/or physiological landmark data from the MET are collected and entered into a data set. For example, performance data collected for a genotype of corn may include any of the following: yield, grain moisture, stalk lodging, stand establishment, emergence, midsilk, test weight, protein, oil, and starch. Yield refers to bushels of grain per acre. Grain moisture refers to a moisture determination made from each plot at harvest time, using an instrument such as an electrical conductance moisture meter. Stalk lodging refers to the determination of the number of broken stalks in each plot prior to harvest. Stand establishment refers to the differences between the desired planting rate for each hybrid and the final stand. Emergence refers to an emergence count made on each plot after plant emergence where emergence percentage may be computed based on the number of plants and the number of kernels planted. The mid silk date is the Julian day of the year in which 50% of the plants show silks at one site in a region. The test weights are typically reported as pounds per bushel on grain samples at field moisture. Protein, oil and starch are typically reported as a percent protein, oil, and starch content at a designated percent grain moisture on dried samples using standard methods, for example, a near infrared transmittance whole grain analyzer.

One skilled in the art would be familiar with performance data collected for other crops, for example, soybeans, wheat, sunflowers, canola, rice and cotton. Performance data for soybeans include, without limitation, relative maturity, plant height, lodging score, seed size, protein and oil percentage, Phytophthora resistance genes, Phytophthora partial resistance, Sclerotinia rating, and yield. Relative maturity refers to a determination that is designed to account for factors, such as soybean variety, planting date, weather, latitude and disease that affect maturity date and number of days from planting to maturity. Plant height refers to a determination of the soybean plant's height, usually determined prior to harvest. Lodging, traditionally, the vertical orientation of the plant, i.e. the degree to which the plant is erect. The lodging of a soybean plant is traditionally rated by researchers using a scale of 1 to 9 as follows: 1.0=almost all plants erect, 3.0=either all plants leaning slightly, or a few plants down, 5.0=either all plants leaning moderately (45 degree angle), or 25-50% down, 7.0=either all plants leaning considerably, or 50-80% down, 9.0=all plants prostrate. The seed size of a soybean plant typically refers to thousands of seeds per pound. Protein and oil percentage analysis may be determined using near infrared transmittance technology and reported at 13% moisture. Phytophthora resistance genes may be determined using a hypocotyl inoculation test with several races of Phytophthora to determine the presence or absence of a particular Rps gene in a soybean plant. Soybeans may also be evaluated for phytophthora partial resistance using a ratings system, where ratings of 3.0 to 3.9 are considered high levels of partial resistance, ratings of 4.0 to 5.9 are considered moderate, ratings over 6.0 indicate very little partial resistance or protection against Phytophthora. Soybeans may also be evaluated for partial resistance to Sclerotinia. Yield refers to bushels per acre at 13 percent moisture.

Typical performance data for wheat includes, without limitation, test weight, protein percent, seed size, percent lodging, plant height, heading date, powdery mildew, leaf blotch complex (LBC), Fusarium head scab (FHS), flour yield, and flour softness. Test weight refers to a determination of pounds/bushell using harvest grain moisture. Seed size refers to thousands of harvested seeds per pound. Percent lodging as described previously refers to a rating system used to estimate the percent of plants that are not erect or lean more than 45 degrees from vertical. Plant height refers to the distance from the soil surface to the top of the heads. Heading date refers to the average calendar day of the year on which 50 percent of the heads are completely emerged. Wheat infected with powdery mildew (PM) may be determined using a scale system where each plot is rated based on a 0 to 10 scale where: 0=0 to trace % leaf area covered; 1=leaf 4 with trace −50%; 2=leaf 3 with 1-5%; 3=leaf 3 with 5-15%; 4=leaf 3 with >15%; 5=leaf 2 with 1-5%; 6=leaf 2 with 5-15%, 7=leaf 2 with >15%; 8=leaf 1 with 1-5%; 9=leaf 1 with 5-15%; and 10=leaf 1 with >15% leaf area covered (leaf 1=flag leaf). This scale takes into account the percentage leaf area affected and the progress of the disease upward on the plants. Leaf blotch complex (LBC) caused by Stagonospora nodorum, Pyrenophora triticirepentis and Bipolaris sorokiniana for example may be determined when most varieties are in the soft dough growth stage and rated based on the percentage of flag leaf area covered by leaf blotches. Fusarium head scab (FHS) caused by Fusarium graminearum for example may be determined when plants are in the late milk to soft dough growth stage and each plot is rated based on a disease severity estimate as the average percentage of spikelets affected per head. Flour yield refers to the percent flour yield from milled whole grain. Flour softness refers to the percent of fine-granular milled flour. Values higher than approximately 50 indicate kernel textures that are appropriate for soft wheat. Generally, high values are more desirable for milling and baking.

Typical performance data for sunflower includes, without limitation, resistance to aphids, neck breakage, brittle snap, stalk breakage, resistance to downy mildew (*Plasmopara halstedii*), height of the head at harvest, seed moisture, head shape, hullability, resistance to the sunflower midge, *Contarinia schulzi*, percentage of oil content, seed size, yield, seedling vigor, and test weight. Resistance to aphids refers to a visual ratings system indicating resistance to aphids based on a scale of 1-9 where higher scores indicate higher levels of resistance. Neck breakage refers a visual ratings system indicating the level of neck breakage, typically on a scale from 1 to 9 where the higher the score signifies that less breakage occurs. Brittle snap refers to a visual rating system indicating the amount of brittle snap (stalk breakage) that typically occurs in the early season due to high winds. The ratings system is based on a scale, usually ranging from 1-9, with a higher score denoting the occurrence of less breakage. A sunflower's resistance to Downy Mildew (*Plasmopara halstedii*) may be determined using a visual ratings scaled system with 9 being the highest and 1 the lowest. A higher score indicates greater resistance. Height of the head at harvest refers to the height of the head at harvest, measured in decimeters. Seed moisture refers to a determination of seed moisture taken at harvest time, usually measured as a percentage of moisture to seed weight. Head shape of a sunflower is measured visually using a scale system where each plot is rated based on a 1 to 9 scale where: 1 =closed "midge" ball; 2=trumpet; 3=clam; 4=concave; 5=cone; 6=reflex; 7=distorted; 8=convex; 9=flat. Hullability refers to the ability of a hulling machine to remove seed hulls from the kernel, typically measured on a 1-9 scale where a higher score reflects better hullability. Resistance to the sunflower midge, *Contarinia schulzi*, is determined based on head deformation which is rated on a 1-9 scale where: 9=no head deformation (fully resistant), 5=moderate head deformation, 1=severe head deformation (fully susceptible). The percentage of oil content from the harvested grain is measured and adjusted to a 10% moisture level. The oil content of a sunflower seed may be measured for various components, including palmitic acid, stearic acid, oleic acid, and linoleic acid, using a gas chromatograph. Seed size refers to the percentage of grain that passes over a certain size screen, usually "size 13." Seedling vigor refers to the early growth of a seedling and is often times measured via a visual ratings system, from 1-9, with higher scores indicate more seedling vigor. Yield is measured as quintals per hectare, while test weight of seed is measured as kilograms per hectoliter.

Typical performance data for canola includes, without limitation, yield, oil content, beginning bloom date, maturity date, plant height, lodging, seed shatter, winter survival, and disease resistance. Yield refers to pounds per acre at 8.5% moisture. Oil content is a determination of the typical percentage by weight oil present in the mature whole dried seeds. Beginning bloom date refers to the date at which at least one flower is on the plant. If a flower is showing on half the plants, then canola field is in 50% bloom. Maturity date refers to the number of days observed from planting to maturity, with maturity referring to the plant stage when pods with seed color change, occurring from green to brown or black, on the bottom third of the pod bearing area of the main stem. Plant height refers to the overall plant height at the end of flowering. The concept of measuring lodging using a scale of 1 (weak) to 9 (strong) is as previously described. Seed shatter refers to a resistance to silique shattering at canola seed maturity and is expressed on a scale of 1 (poor) to 9 (excellent). Winter survival refers to the ability to withstand winter temperatures at a typical growing area. Winter survival is evaluated and is expressed on a scale of 1 to 5, with 1 being poor and 5 being excellent. Disease resistance is evaluated and expressed on a scale of 0 to 5 where: 0=highly resistant, 5=highly susceptible. The Western Canadian Canola/Rapeseed Recommending Committee (WCC/RRC) blackleg classification is based on percent severity index described as follows: 0-30% =Resistant, 30%-50% =Moderately Resistant, 50%-70% =Moderately Susceptible, 70%-90% =Susceptible, and >90% =Highly susceptible.

Typical performance data for cotton includes, without limitation, yield, turnout, micronaire, length, fiber strength of cotton and color grade. Yield is measured as pounds per acre. Turnout refers to lint and seed turnout which is calculated as the percentage of lint and seed on a weight basis as a result of ginning the sub sample from each treatment. Micronaire refers to fiber fineness and maturity and are measured using air flow instrument tests in terms of micronaire readings in accordance with established procedures. Fiber length is reported in 1/32 of an inch or decimal equivalents. Fiber strength is measured in grams per tex and represents the force in grams to break a bundle of fibers one tex unit in size. Color grade for cotton takes into consideration the color, fiber color and whiteness of cotton leaves. Color grade may be determined using a two digit scale. The two digit number is an indication of the fiber color and whiteness (i.e. 13, 51, or 84). The first digit can range from 1 to 8 representing overall color with 1 being the best color and 8 representing below grade colors. The second digit represent a fiber whiteness score. This number ranges from 1 to 5, with 1 representing good white color and 5 representing yellow stained. The second number in the overall color grade represents the leaf score and represents leaf content in the sample.

Typical performance data for rice includes, without limitation, yield, straw strength, 50% Heading, plant height, and total milling, and total milling. Yield is measured as bushels per acre at 12% moisture. Straw Strength refers to lodging resistance at maturity and is measured using a numerical rating from 1 to 9 where 1=Strong (no lodging); 3=Moderately strong (most plants leaning but no lodging); 5=Intermediate (most plants moderately lodged); 7=Weak (most plants nearly flat); and 9=Very weak (all plants flat). 50% heading refers to the number of days from emergence until 50% of the panicles are visibly emerged from the boot. Plant height is the average distance from the soil surface to the tip of erect panicle. Total milling refers to the total milled rice as a percentage of rough rice. Whole milling refers to rice grains of 3/4 length or more expressed as a percentage of rough rice.

The environmental and physiological landmark data may be historical using historical meteorological information along with soils and other agronomic information or collected using National Oceanic and Atmospheric Association and/or other public or private sources of weather and soil data. Potential environmental and physiological landmark data that may be collected includes but is not limited to wind, drought, temperature, solar radiation, precipitation, soil type, soil pH, planting and harvesting dates, irrigation, tiled area, previous crop, fertilizer including nitrogen, phosphorous, and potassium levels, insecticide, herbicide, and biotic data, for example, insects and disease. The environmental and physiological landmark data may then be analyzed in light of genotype performance data to determine G×E interactions.

Models

Several models for determining G×E interactions exist. Base models group or classify the locations used to test the hybrids, include several variance components, and stratify the hybrids, for example, according to locations among station-year combinations, locations, or other chosen variances.

For example, as shown in Table 1, one base model Year Station (YS) groups the locations by year-stations where a year-station designates a unique site or location by year. Other variances include blocks within locations within year-stations, hybrids, hybrids by year-station divided by the sum of hybrids by locations within year station locations as well as a residual. The YS model is disadvantageous in that a given location's environment will vary over time so that the G×E information gleaned from the model may not be relevant for predicting hybrids that will perform well in the same location next year.

Another model for determining G×E interactions disclosed in Table 1, groups different sites by location. Other variances for the G×E model include blocks within locations, hybrids, hybrids by locations, as well as a residual. However, the G×E model is disadvantageous in that a genotype grown in locations with differing environmental conditions may have similar performance results, complicating the analysis of the specific environmental conditions that play a role in contributing to genotype performance and reducing the certainty of predicting product performance.

Unlike the previous models mentioned, the present inventors contemplate determining G×E interactions using a model referred to herein as Environmental Classification that groups locations by environmental classifications. Thus, variances for this model include locations within environmental classifications, blocks within locations within environmental classifications, hybrids, hybrids by environmental classifications divided by hybrids by locations within environmental classifications and a residual.

TABLE 1

Models for determining G × E interactions

| Model | Year-Station | G × E | Environmental Classification |
|---|---|---|---|
| Variance for location | Location within year-station | Location | Location within environmental classification |
| Variance for location | blocks within locations within year-station | blocks within locations | blocks within locations within environmental classifications |
| Variance for hybrids | hybrids | hybrids | hybrids |
| Stratifications | hybrid by year-station/hybrids by locations within locations | hybrid by locations | hybrid by environmental classifications/ hybrid by locations within environmental classifications |

Burdon has shown that genetic correlation between G×E interactions can be estimated. (Burdon, R. D. 1977. Silvae Genet., 26: 168-175.). G×E analysis may be performed in numerous ways. G×E interactions may be analyzed qualitatively, e.g. phenotype plasticity, or quantitatively using, for example, an analysis of variance approach. (Schlichting, C. D. 1986. Annual Review of Ecology and Systematics 17: 667-693.). Statistical analysis of whether a G×E interaction is significant and whether environmental changes influence certain traits, such as yield performance, of the genotypes evaluated may be performed using any number of statistical methods including but not limited to, rank correlation, analysis of variances, and stability.

Rank Correlation

Figure 2A:
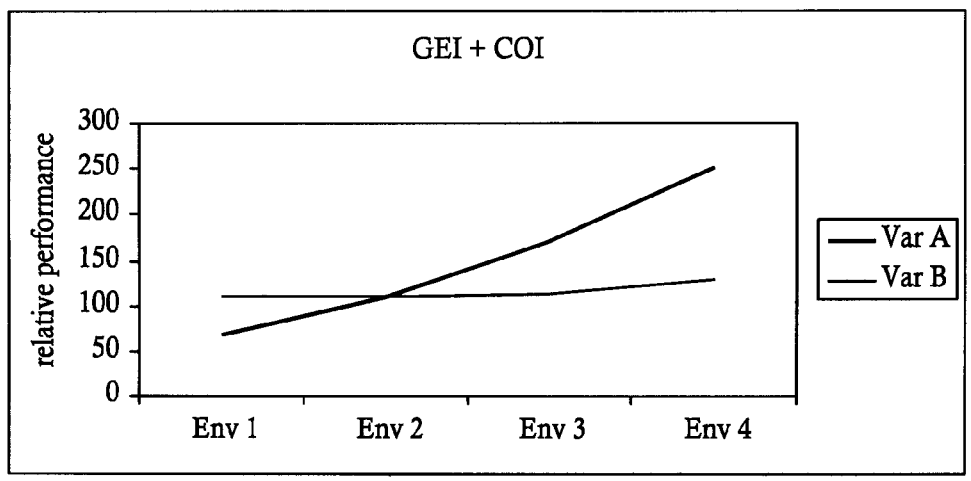
FIG. 2A to FIG. 2C provide an example of genotype by environment interactions and cross-over interactions between two different varieties in four different environmental classes.
Figure 2B:
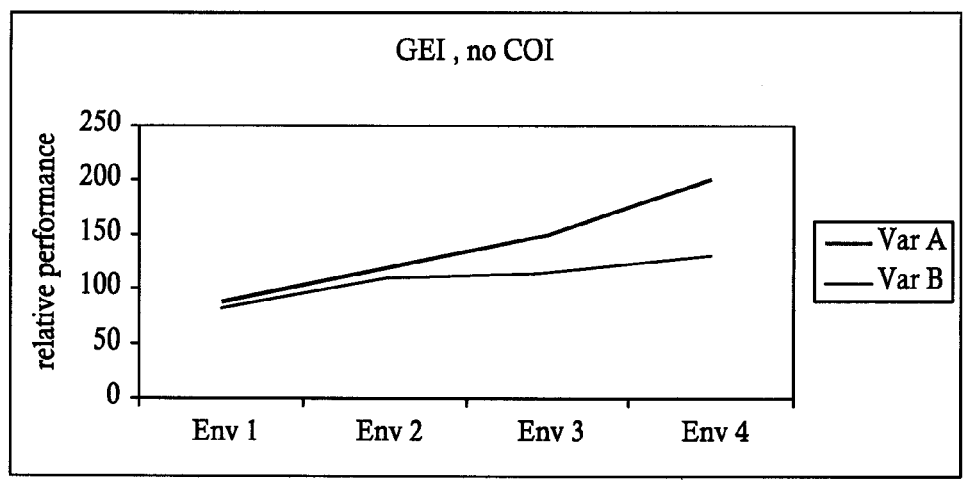
Figure 2C:
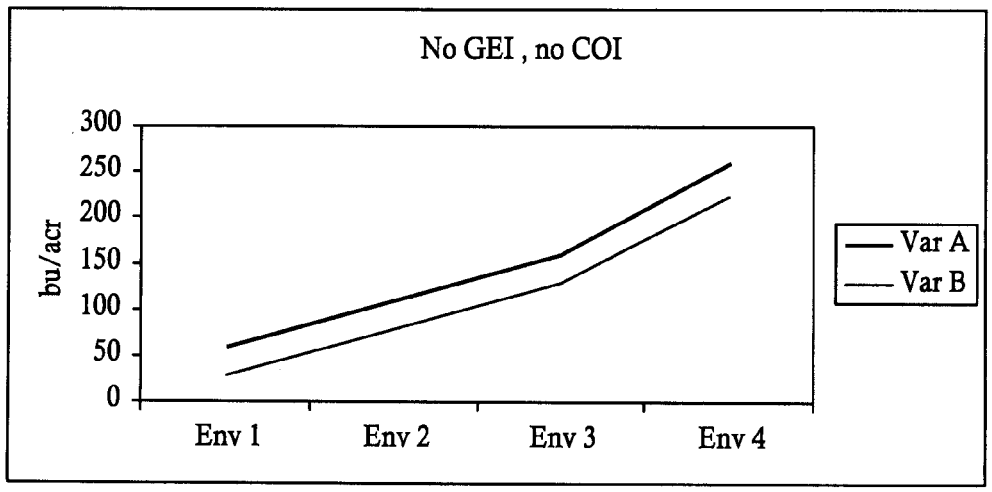

The most basic categorization of G×E interaction is to evaluate G×E interactions by performing a rank correlation according to standardized tests, for example, Spearman. The Spearman rank correlation may be performed to examine the relationships among genotypes in different environments, for example, crossover interactions that occur when two genotypes change in rank order of performance when evaluated in different environments. FIG. 2 illustrates an example of G×E interactions and cross-over interactions (COI) between two different varieties, Var A and Var B, in four different environmental classes, Env 1, Env 2, Env 3 and Env 4. FIG. 2A shows that Var A and Var B out-perform each other in different environments indicating the occurrence of both G×E and COI. FIG. 2B shows that Var A performed better than Var B in each environment, indicating G×E interactions but no COI. In contrast, FIG. 2C shows that Var A and Var B each performed consistently with respect to each other in all four environments, indicating lack of G×E interactions.

Analysis of Variance (ANOVA)

Figure 3:
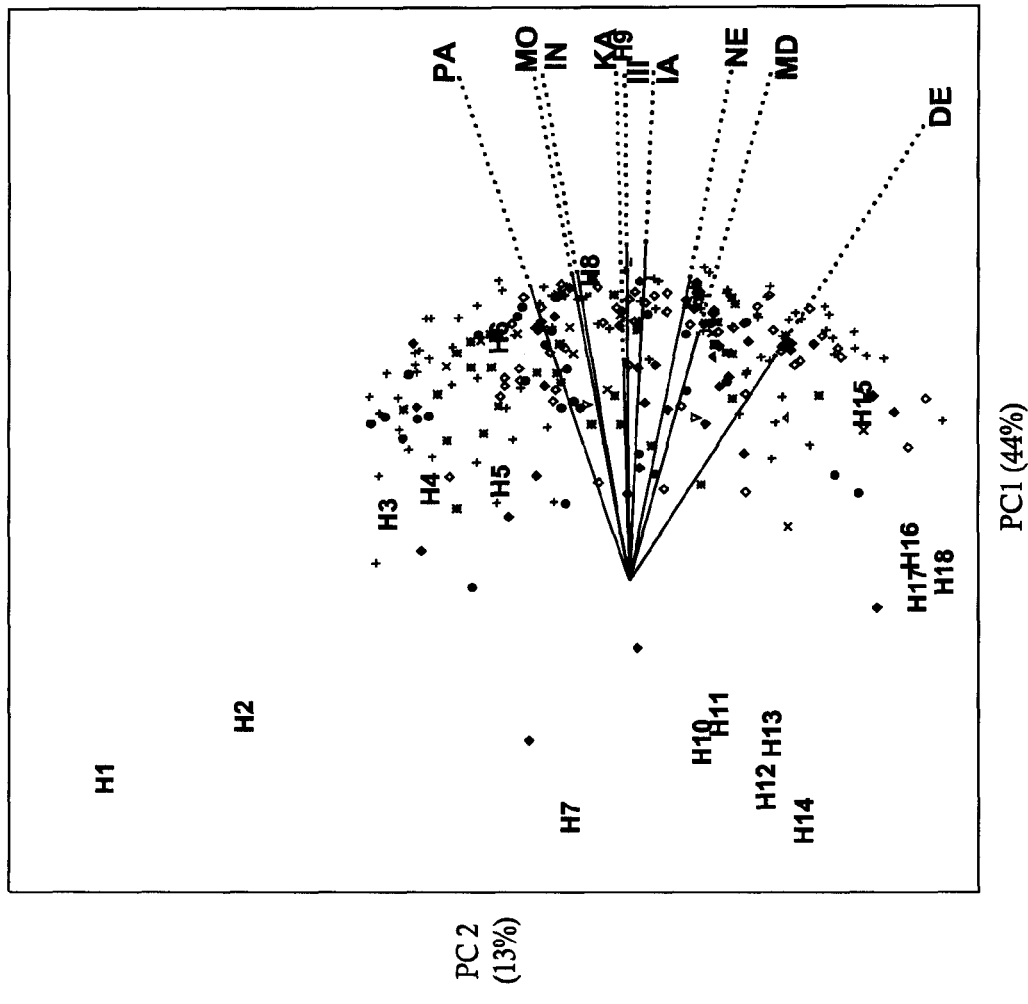
FIG. 3 illustrates environment-standardized GGE biplot of grain yield of 18 maize hybrids (H1-H18) grown in 266 environments over three years stratified by state.
Figure 4:
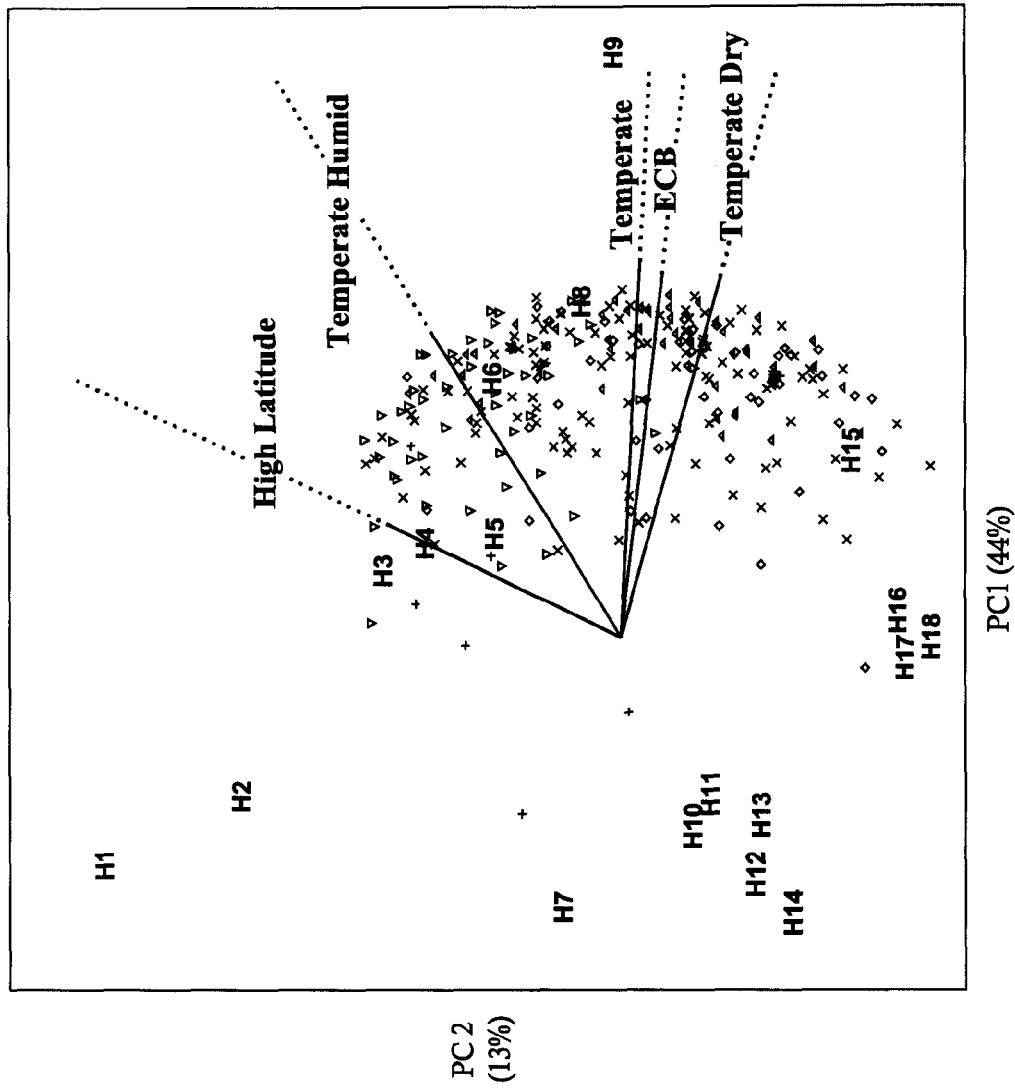
FIG. 4 illustrates environment-standardized GGE biplot of grain yield of 18 maize hybrids (H1-H18) grown in 266 environments over three years stratified by environmental class.

Alternately, G×E interactions may be analyzed using an analysis of variance method (ANOVA) (Steel, R. G. D and J. H. Torrie. 1980. Principles and Procedures of Statistics, 2nd edition) over environments to determine the significance of genotypes, environments and G×E interactions. G×E interactions may also be analyzed using ASREML (Gilmour, A. R., Cullis, B. R., Welham, S. J. and Thompson, R. 2002 ASReml Reference Manual 2nd edition, Release 1.0 NSW Agriculture Biometrical Bulletin 3, NSW Agriculture, Locked Bag, Orange, NSW 2800, Australia.) for the computation of variance components, and the generation of GGE biplots (Cooper, M., and I. H. DeLacy. 1994. Theor. Appl. Genet. 88:561-572; Yan, W. and M. S. Kang. 2003. *GGE Biplot Analysis: A Graphical Tool for Breeders Geneticists, and Agronomists*. CRC Press. Boca Raton, Fla.). FIG. 3 and FIG. 4 illustrate environment-standardized GGE biplot of grain yield of 18 maize hybrids (H1-H18) grown in 266 environments over three years, stratified by state or by environmental class respectively.

Stability

Once certain genotypes are identified that perform well in a target environment they may be analyzed to determine which hybrids are more stable in yield or other metrics using various methods. One method uses a regression of genotypic performance on an environmental index. In general, the environmental index is the deviation of the mean phenotype at environment from the overall mean phenotype of all environments. Thus, the phenotype of an individual genotype with each environment is regressed on the environmental index, as described in Bernardo R. 2002. Quantitative Traits in Plants. Stemma Press, Woodbury, Minn. to generate a slope (b-value) for each genotype/cultivar evaluated. Other methods include the joint regression analysis method proposed by Perkins, J. M. and Jinks, J. L. 1968. Heredity. 23: 339-359, Finlay, K. W. and Wilkinson, G. N. 1963. Aust. J. Res. 14: 742-754 and Eberhart, S. A. and Russell, W. A. 1966. Crop Sci. 6:36-40 to calculate the regression coefficient (b), S.E. and variance due to deviation from regression (S2d) as a parameter of stability and adaptability. The model described by Eberhart and Russell has the following formula:

$$P_{ij} = \mu + g_i + b_i t_j + \delta_{ij} + e_{ij}$$

where $P_{ij}$ is the mean phenotype of genotype or cultivar i in location j, $\mu$ is the grand mean across the whole experiment for all genotypes and locations, $g_i$ is the effect of genotype i across all locations $b_i$ is the linear regression of $P_{ij}$ on $t_j$, $t_j$ is the environmental index, that is the effect of environment j across all genotypes), $\delta_{ij}$ is the deviation $P_{ij}$ from the linear regression value for a given $t_j$ and $e_{ij}$ is the within environment error.

Categorization of Land Bases into Environmental Classes

Figure 5:
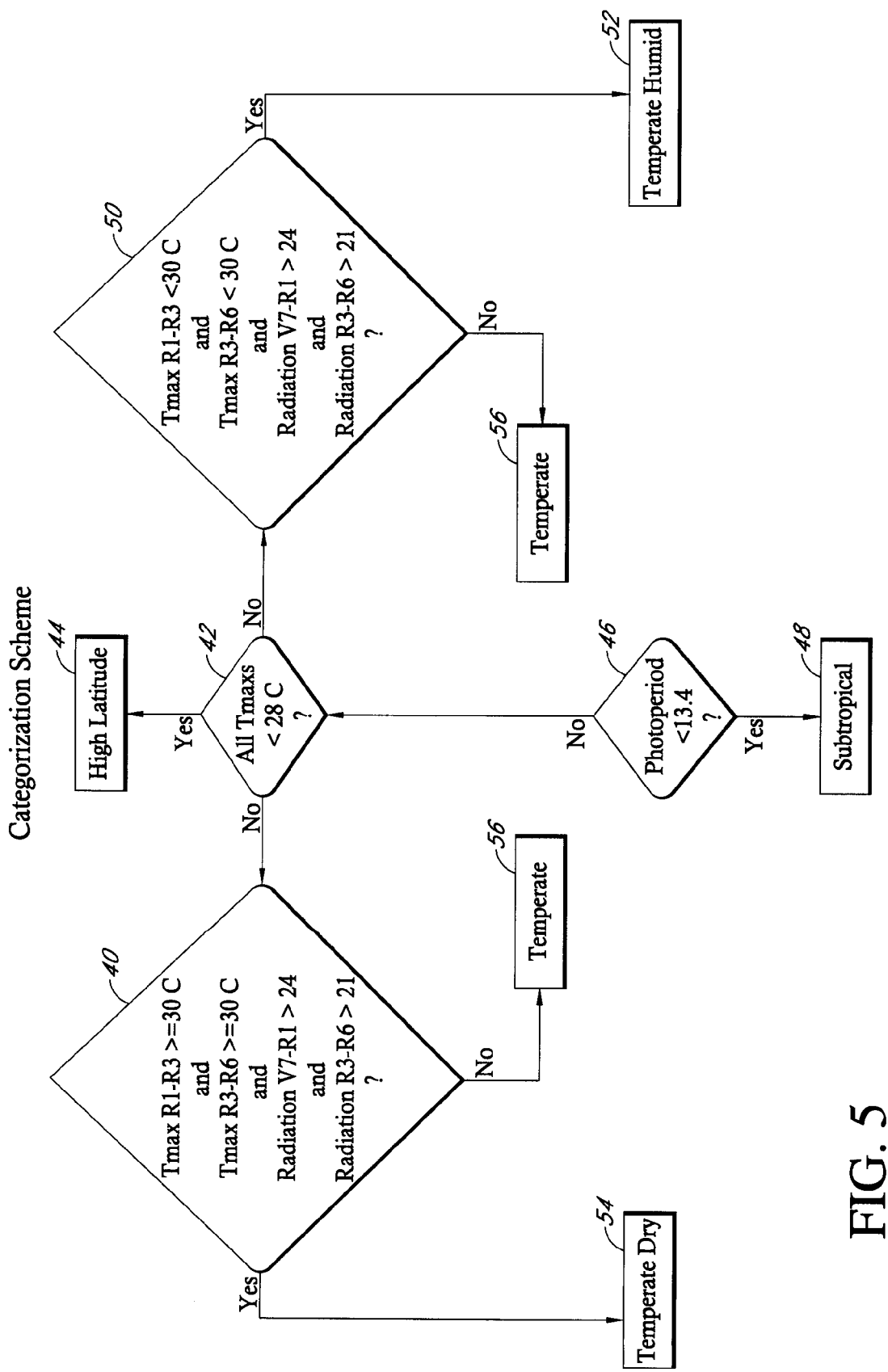
FIG. 5 illustrates one possible schematic for categorizing different land bases into environmental classifications based on temperatures, solar radiation, and length of photoperiod.

Using the information collected for or from G×E analysis, the land bases may be categorized into environmental classifications. FIG. 5 illustrates one possible schematic for categorizing different land bases into environmental classifications. With reference to FIG. 5, one method of categorizing environmental classifications is illustrated as a flow chart. If all maximum temperatures are greater than 28° Celsius 42, then the land base may be categorized as either Temperate Dry 54, Temperate Humid 52, Temperate 56, or Subtropical 48. If all maximum temperatures are greater to or equal to 30° Celsius and solar radiation is greater than 24 and 21 at a given crop development stage, e.g. v7-R1, R3-R6 40, then the land base is characterized as Temperate Dry 54. If the maximum temperature is not greater than or equal to 30° Celsius and solar radiation is not greater than 24 at a given crop development stage, e.g. V7-R1 and 21 for R3-R6 respectively 40, then the land base is characterized as Temperate 56. However, if the maximum temperature is less than 30° Celsius and solar radiation is greater than 24 and 21 at a given crop development stage 50, then the land base is characterized as Temperate Humid 52. If the maximum temperature is not less than 30° Celsius and solar radiation is not greater than 24 and 21 at a given crop development stage 50, then the land base is characterized as Temperate 56. If all maximum temperatures 42 for the land base are less then 28° Celsius than the land base is characterized as High Latitude 44. In contrast, if all maximum temperatures 42 for the land base are not less then 28° Celsius and the land base has a photoperiod less than 13.4 hours/day 46, then the land base is Subtropical 48.

Figure 6:
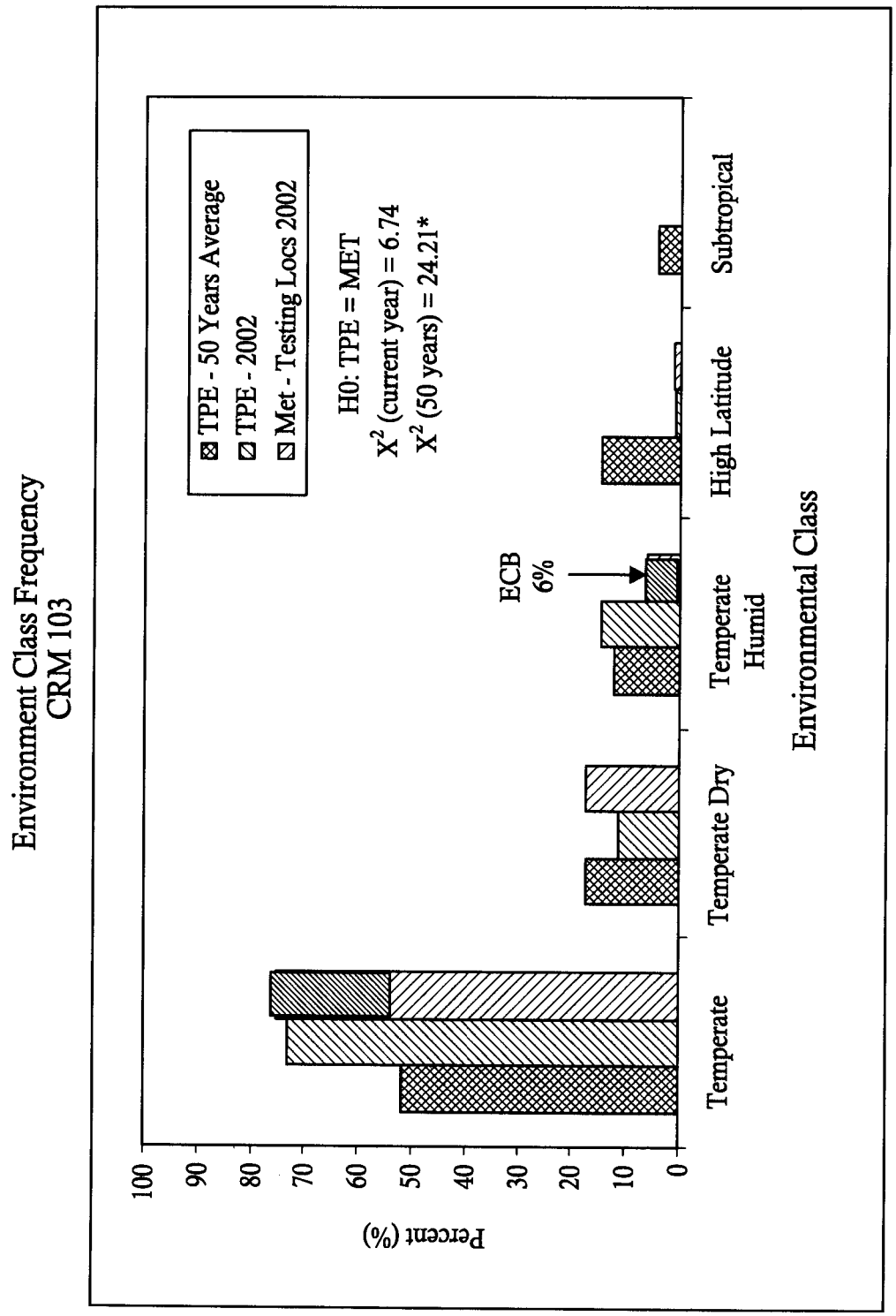
FIG. 6 is a bar graph representation of the frequency of various environmental classes among target population of environments (TPEs) or multi-environment trials (METs).
Figure 7:
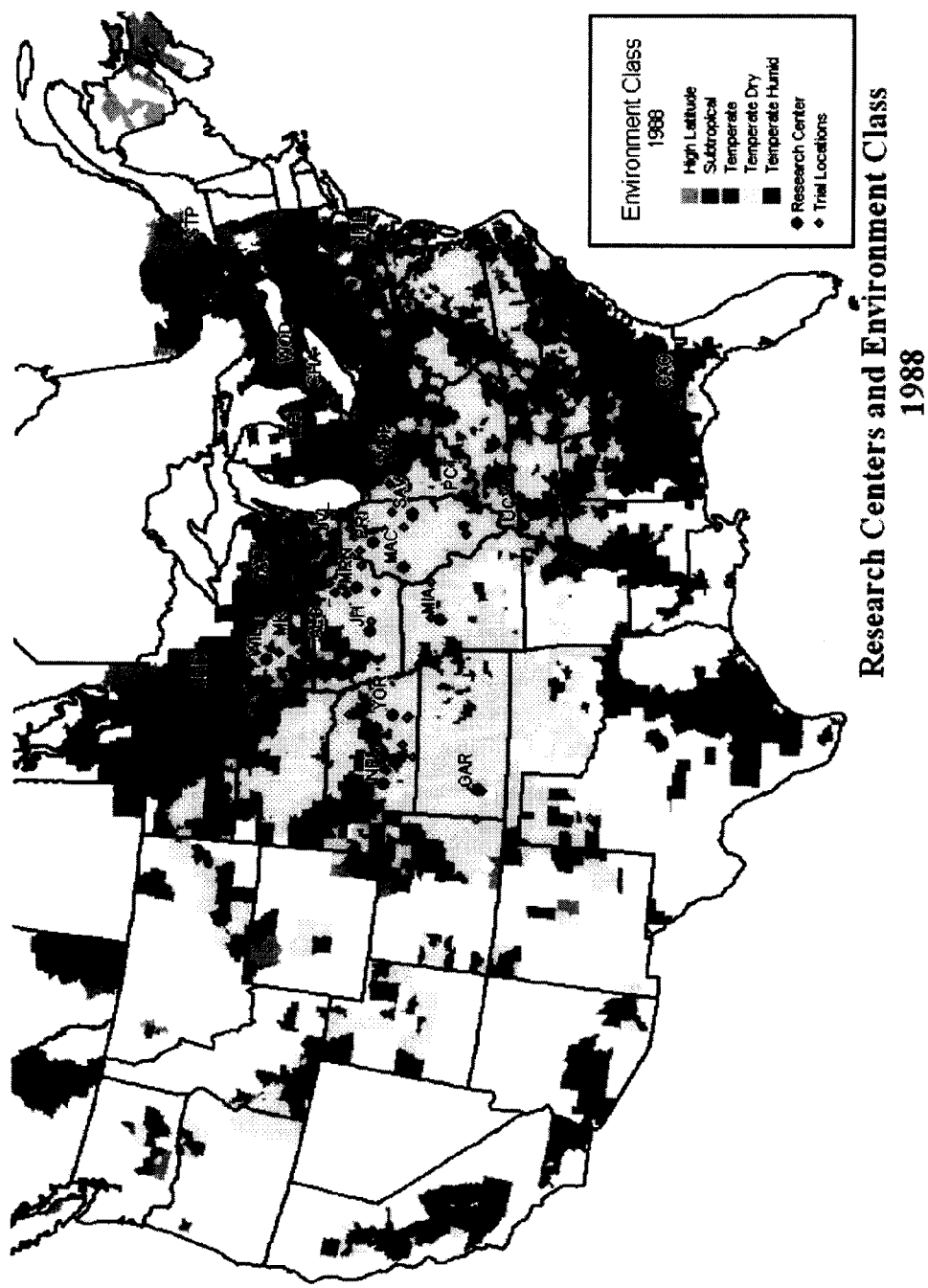
FIG. 7 illustrates potential categories of environmental classes identified throughout the United States in 1988 and their locations; these include temperate, temperate dry, temperate humid, high latitude, and subtropical classes.

Categorizing land bases into environmental classifications has several advantages. First, environmental classifications can bring an understanding of the various environments under which crops are produced. Second, occurrence probabilities for each environmental category can be assigned to each geographic location and the frequency of the classifications determined using routine methods. FIG. 6 is a bar graph representation of the frequency of various environmental classes among TPEs or METs. The frequency for each environmental class, e.g. temperate, temperate dry, temperate humid, high latitude, and subtropical, is given as a percent of the total TPE or MET tested in given year or across years. FIG. 7 illustrates potential categories of environmental classes identified throughout the United States in 1988 and their locations; these include temperate, temperate dry, temperate humid, high latitude, and subtropical classes. It will be apparent to one skilled in the art that other environmental classifications may added as identified or deemed relevant to G×E interactions for various crops.

Some of the environmental classification may be defined using general characteristics of climates. For example, temperate may be used to refer to regions in which the climate undergoes seasonal change in temperature and moisture; typically these regions lie between the Tropic of Capricorn and Antarctic circle in the Southern Hemisphere and between the Tropic of Capricorn and the Arctic circle in the Northern Hemisphere. Temperate humid may refer to regions in which the climate undergoes seasonal change in temperature and moisture and has more humidity than a temperate environment. High latitude as an environmental class may refer to regions that have a longer photoperiod than and is typically north of a particular latitude. A subtropical class may refer to regions enjoying four distinct seasons usually with hot tropical summers and non-tropical winters with a shorter photoperiod/day length; typically these regions lie between the ranges 23.5-40° N and 23.5-40° S latitude. The environmental classes may also be defined by biotic factors, such as diseases, insects, and/or characteristic of a plant. For example, an ECB class may refer to regions having European Corn Borers (ECB) or the suspected presence of ECB as evidenced by preflowering leaf feeding, tunneling in the plant's stalk, post flowering degree of stalk breakage and/or other evidence of feeding. The environmental class Brittle may be used to refers to regions where stalk breakage of corn occurs or is apt to occur near the time of pollination and is indicative of whether a hybrid or inbred would snap or break near the time of flowering under severe winds.

It is to be understood that the environmental classifications may be used and defined differently for different crops/genotypes and that these definitions may vary from year to year, even for the same crops or genotypes. For example, in 2000-2003, trials conducted studying G×E interactions among Comparative Relative Maturity (CRM) hybrids of CRM 103-113 in different environments identified seven different environmental classes—temperate, temperate dry, temperate humid, high latitude, subtropical, ECB, and brittle. For the study purposes, temperate was identified/defined as having a low level of abiotic stresses, a growing season adequate for CRM 103-113, and found to be frequent in Iowa and Illinois. Temperate dry was defined as temperate with some level of water and/or temperature stress and found to be frequent in Nebraska, Kansas, and South Dakota. Temperate Humid was defined as similar to the temperate environmental class but had a complex of biotic factors, such as leaf disease, that may differentially affect product performance. Temperate humid was also characterized as having a temperature and solar radiation lower than that identified in the temperate environmental class and found to be frequent in Indiana, Ohio, and Pennsylvania. The High Latitude environmental class was found to grow corn CRM 103 and earlier (growing hybrids) and experienced colder temperatures than the Temperate environmental class but with longer day-length. This environmental class was found to be frequent in Canada, North Dakota, Minnesota, Michigan, and Wisconsin. The fifth environmental class, Subtropical, was characterized as warm and humid with a short day-length and found frequently in the Deep South of the United States. Another environmental class identified was European Corn Borers (ECB) and defined as having *Bacillus thuringiensis* (Bt) hybrids that outyielded base genetics by at least 10%. The last environmental class Brittle defined areas with significant brittle damage with differential effect on products.

Once areas of land are categorized as environmental classes, these areas may be used in METs. Ultimately, the observed genotype performances in METs can be linked by the environmental class to the TPE. By evaluating product performance in a target environment, rather than merely performance differences in METs, genotype performance data from multiple test environments can be correlated to a target environment and used to predict product performance. This correlation between a genotype's performance and the target environment or environmental classification will lead to more precise product placement since the genotype performance is characterized within an environmental class in which it is adapted and most likely to experience after commercialization, consequently resulting in improved and more predictable product performance. The analysis of G×E interactions facilitates the selection and adoption of genotypes that have positive interactions with its location and its prevailing environmental conditions (exploitation of areas of specific adaption). G×E analysis also aids in the identification of genotypes with low frequency of poor yield or other performance issues in certain environments. Therefore, G×E analysis will help in understanding the type and size of G×E interactions expected in a given region. The present inventors contemplate that proper selection of hybrids for a particular land base will improve agricultural potential of certain geographic areas by maximizing the occurrence of crop performance through the use of the environmental classification. In addition, this approach allows the use of statistical and probability based analysis to quantify the risk of product success/failure according to the frequency of environment classes and the relative performance of genotypes within each environment class. This early identification and selection of hybrids would enable seed producers to start seed production and accelerate the development of hybrids in winter nurseries in warmer southern climates.

Moreover, environmental classification allows for the creation of an environmental profile for all or any part of the land base classified. Environmental classifications can be determined for each producer's land base. Similarly, the environmental performance profile of cultivars/hybrids can be determined through field experimentation or predicted using G×E analysis. In combining environmental classification frequencies for a particular land base and product performance by environmental classification, performance measurements are given the appropriate amount of relevance or weight for the land base in question. For example, the data are weighted based on long-term frequencies to compute a prediction of hybrid performance.

Use of G×E in Producer's Selection

According to another aspect of the present invention, a method of using information that documents the environmental profile over time of a crop producer's land base, the environmental performance profile of crop cultivars, and the producer's objectives to select a portfolio of cultivars that maximizes and quantifies the probability that the producer's objectives for productivity will be met. Environmental classification can be used to assist in this process.

Environmental classification can be used to determine the primary environmental drivers of G×E interaction in crops such as corn. That is, what are the primary environmental factors that cause change in the relative performance of hybrids. With this knowledge, crop production areas can be categorized into environmental frequency classes. Within these classes, hybrids tend to perform (as measured by yield) relatively similar to one another. Across these classes, the relative performance of hybrids tends to be significantly different. Using historical meteorological information along with soils, pests, and other agronomic information, the frequency of these environments can be determined. This allows the creation of an environmental profile for all or any part of the geography classified. That is, a frequency distribution of the occurrence of the key Environment Classes. This can be done for each crop producer's land base.

Similarly, the environmental performance profile of crop cultivars can be determined through field experimentation. That is, a description of relative performance of cultivars can be determined in each of the key environment classes. In combining Environment class frequencies for a particular land area and product performance by Environment Class, performance measurements are given an appropriate amount of relevance or weight for the land area in question Thus, this aspect of the invention involves combining of this information at the producer's level to optimize crop productivity in such a way that it maximizes the probability of the producer's business operation reaching its productivity goals. The present invention contemplates that information can be used from any number of classification schemes to the selection of cultivars with the objective of maximizing the probability of attainment of the productivity and business goals of a crop producer's operation.

The approach of this aspect of the present invention does so by using compiled long term geo-referenced weather, soils, and agronomic data including biotic factors for the producer's land base to categorize the land base in terms of how frequently annual environmental variation occurs to a degree that is likely to impact relative hybrid performance. In addition, it can incorporate the producer's business objectives including, but not limited to preparedness to take risk. The present invention is able to combine environmental variability with producer business information to create a producer profile. Product performance information stratified by the same criteria is used to define the producer's environmental profile (for example, environmental classes) which is then integrated with the producer's profile.

The relative hybrid performance information that is relevant to the producer's land base is used regardless of when and where it was generated. The present inventors are first to predict future performance of genotypes and quantify probability/risk associated with that performance using data from environments that are considered to be substantially equivalent in terms of relative hybrid response. The result is a more robust and predictive data set thus allowing more informed product selection decisions that, over time will result in a higher probability of a producer operation meeting business objectives for productivity.

Figure 8:
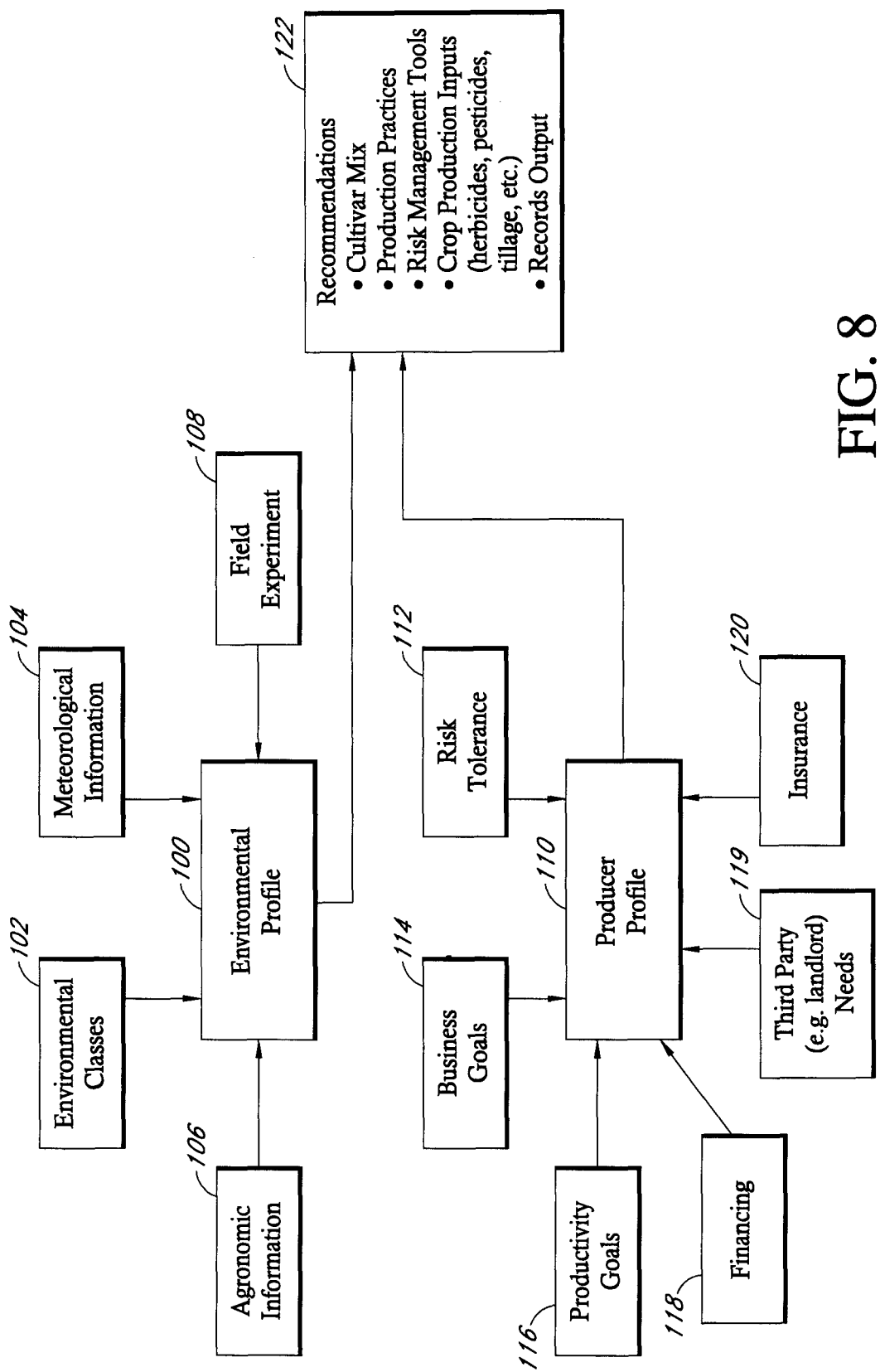
FIG. 8 is a flow diagram illustrating information flow from an environmental profile and a producer profile to providing recommendations to a producer according to one embodiment of the present invention.

FIG. 8 illustrates information flow according to one embodiment of the present invention. In FIG. 8 there is an environmental profile 100. The environmental profile can be based on one or more inputs such as environment classes 102, meteorological information 104, agronomic information 106, or field experimentation 108. In FIG. 1 there is also a producer profile 110. The producer profile 110 is based on one or more inputs such as risk tolerance 112 of the producer, business goals 114 of the producer, productivity goals 116, financing 118 considerations, third party needs 119, for example a landlord, or insurance/risk management and marketing 120 considerations. The environmental profile 100 the producer profile 110 are combined in order to produce recommendations 122. The recommendations 122 can include risk management tools, a recommended seed product, a recommended mix of seed products, production practice recommendations, such as chemical application information, or any number of other specific recommendations as may be appropriate based on the particular environmental profile 100 and producer profile 110.

Figure 9:
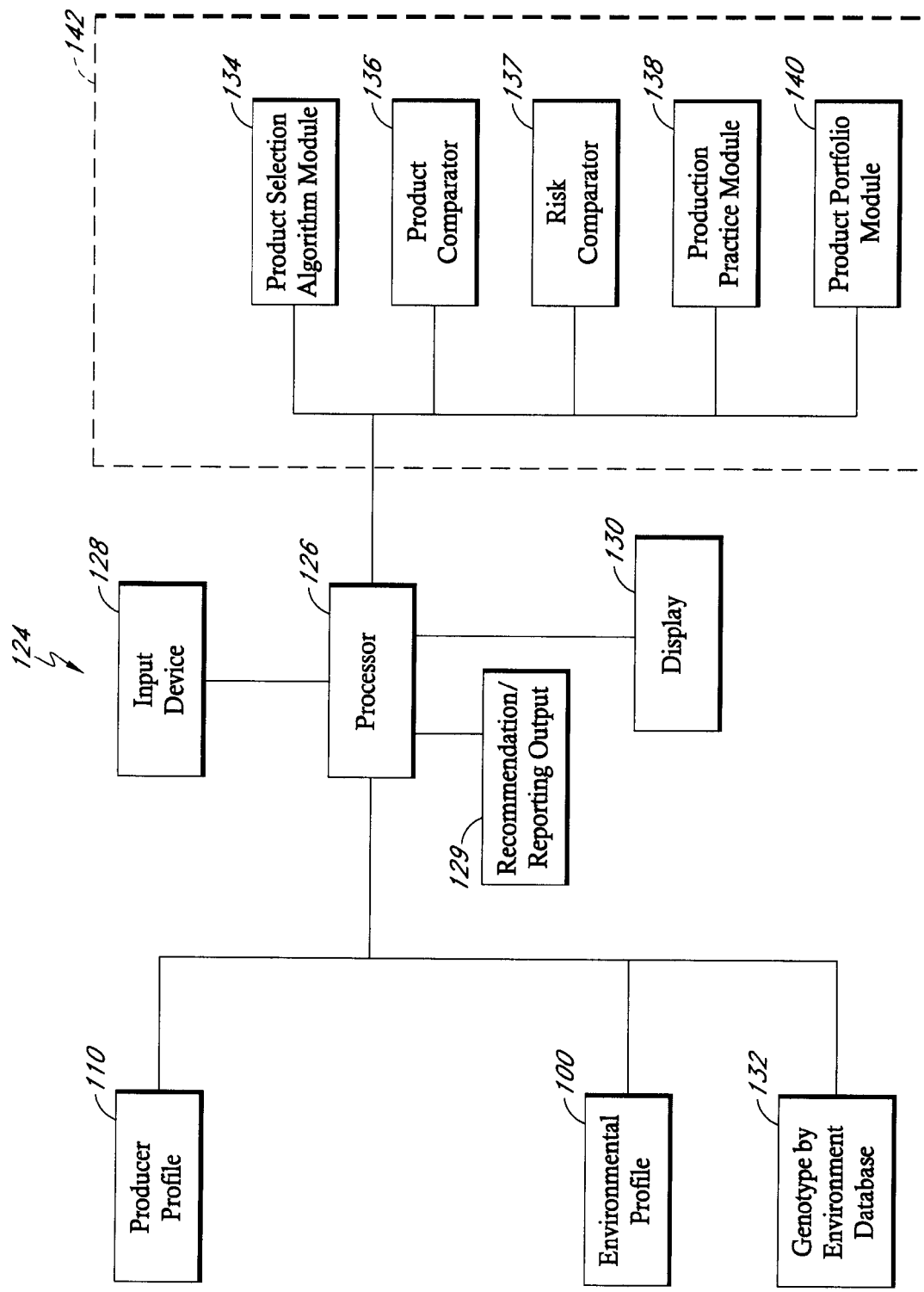
FIG. 9 is block diagram illustrating a system for determining product recommendations according to one embodiment of the present invention.

FIG. 9 illustrates one embodiment of a system 124 for producing product recommendations. In FIG. 9, a processor 126 accesses information associated with a producer profile 110, an environmental profile 100, and a genotype by environment database 132. There is an input device 128, a recommendation output 129, and a display 130 operatively connected to the processor. The present invention contemplates that the processor 126 can be associated with a computer such as handheld computer as may be convenient for a dealer or sales agent. The present invention also contemplates that the producer profile 110, environmental profile 100, and genotype by environment database 132 may be accessible over a network, including a wide-area network such as the Internet.

Using the information in the producer profile 110, environmental profile 100, and genotype-by-environment database 132, the processor applies one or more of a product selection algorithm module 134, a product comparator 136, a production practice module and a risk comparator 138, and a product portfolio module 140. These and/or other modules are collectively the recommendation logic 142. In a simple case, the product selection algorithm module 134 would take information from the environmental profile 100, such as an environmental classification ("Temperate", for example) in addition to information from the producer profile 110, such as a producer objective ("Maximize Yield", "Risk Minimization", "Low Harvest Moisture" for example) and match these criteria to products in the genotype-by-environment database 132. Of course, more specific criteria could be examined as would be the case with more complex environmental profile information and more complex producer profile information.

Figure 10:
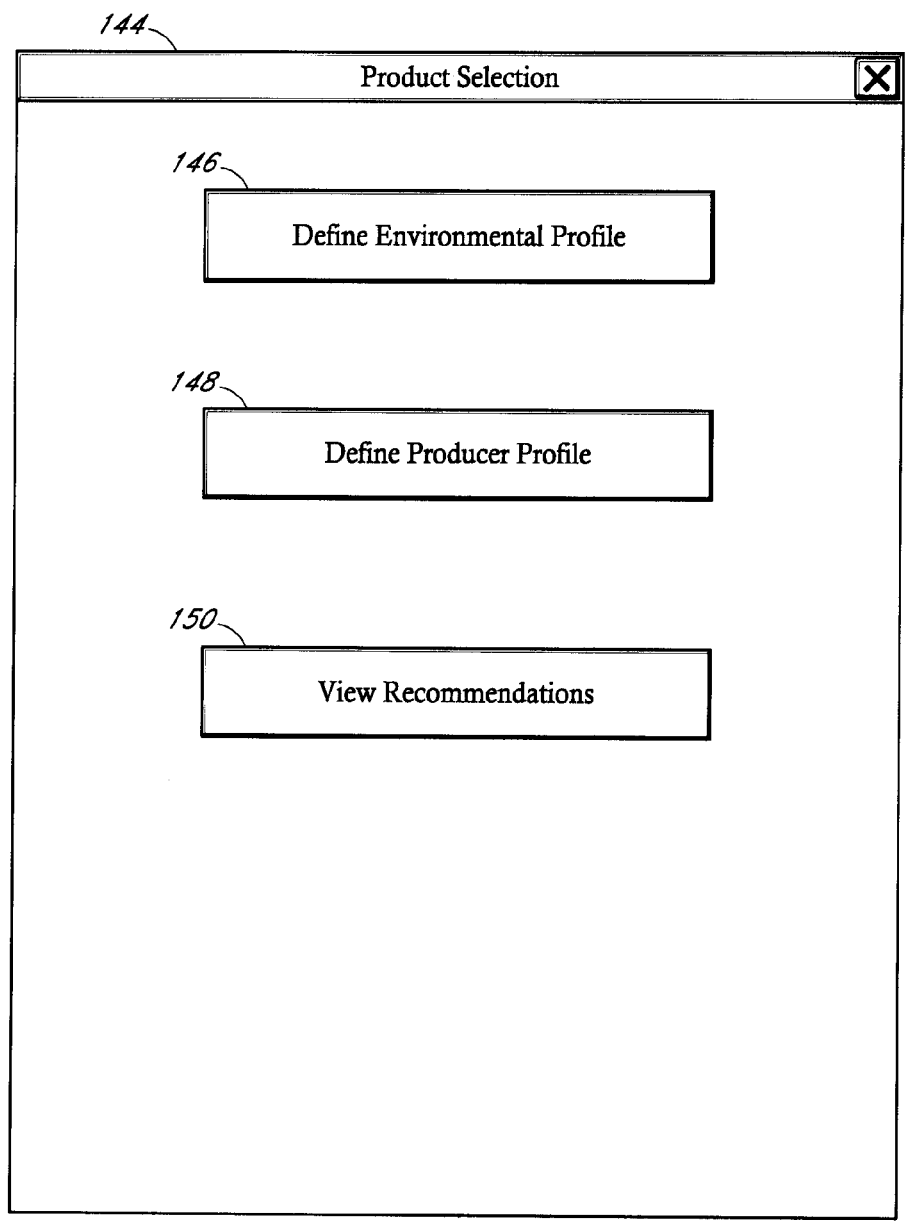
FIG. 10 is a screen display according to one embodiment of the present invention.

FIG. 10 illustrates one embodiment of a screen display 144 of a software application the present invention. In FIG. 10, a user is given the choice of selecting "DEFINE ENVIRONMENTAL PROFILE" 146, "DEFINE PRODUCER PROFILE" 148, and "VIEW RECOMMENDATIONS" 150. Of course, the present invention contemplates that software and its accompanying user interface can be implemented in any number of ways.

FIG. 11 illustrates one embodiment of a screen display 152 of a software application of the present invention. In FIG. 11, a recommendation is given which includes a plurality of products 154, an associated number of acres 156 associated with each of the products, a risk/probability assessment 157, and a recommended crop revenue assurance 158. The present invention provides for decreasing the amount of risk associated with selection of a particular seed product by instead selecting multiple products with different G×E interactions in order to reduce risk associated with environmental variations. The resulting selection, is somewhat akin to selection of stocks in a stock portfolio.

Figure 13:
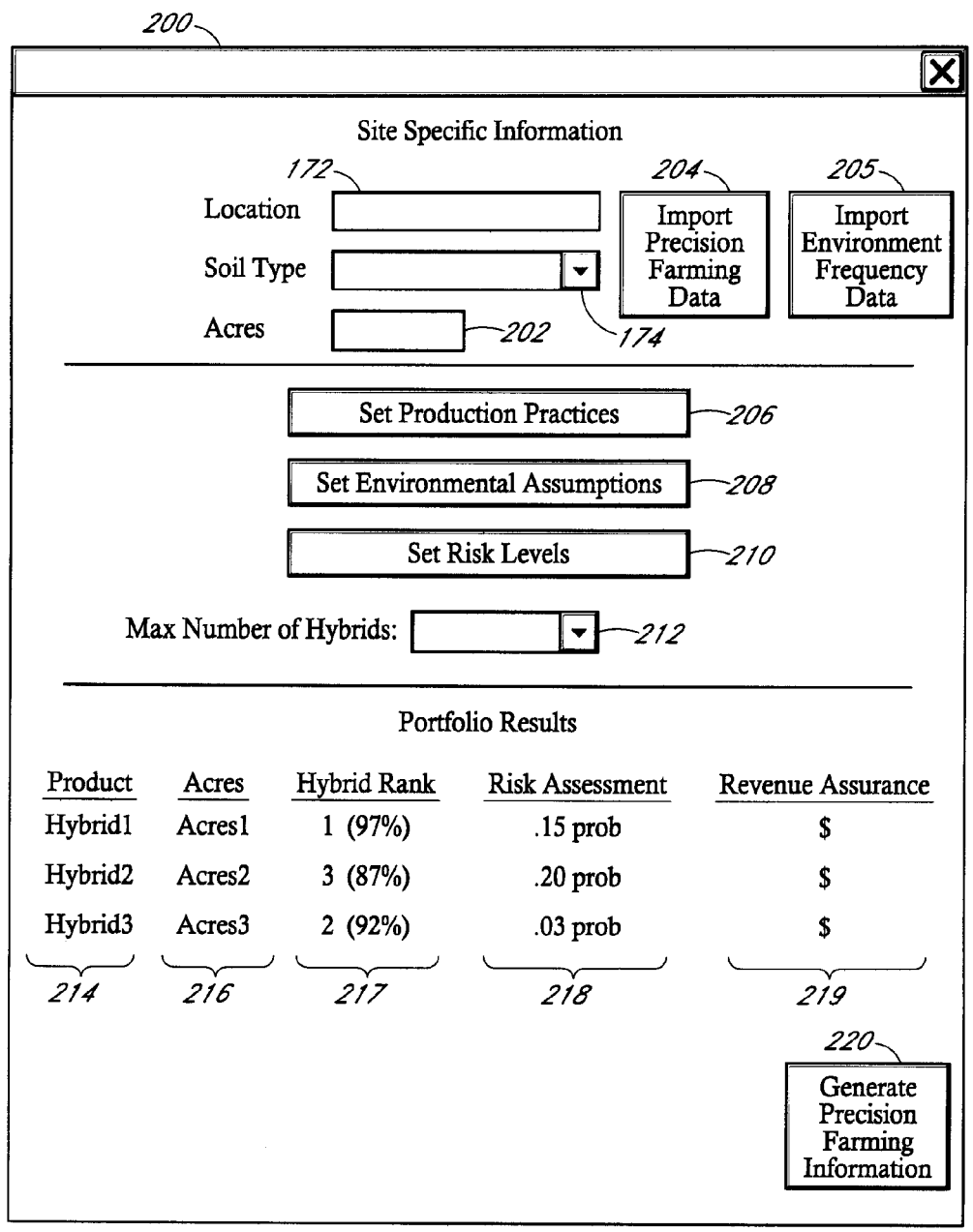
FIG. 13 is a screen display for one embodiment of an application of the present invention.

FIG. 12 and FIG. 13 illustrate embodiments of user interfaces to use in precision farming applications. In FIG. 12, the user interface 170 includes site-specific information associated with location information 172. The present invention contemplates that other site-specific information or historical information is accessible based on the location information 172 and may be used in product selections. In addition, environment and production information is collected. Examples of such information includes maturity days 176, input traits 178, output traits 180, seed treatment 182, the tillage practices 174 used, the planting population 184, nitrogen utilization 186, and drought impact based on environmental classification drought frequency information 187 and soil type. In addition, field attribute information 185 may also be provided. Field attribute information may include crop history, soils, or other field attribute information. Based on this information and information associated with the location 172, a recommendation 188 of at least one hybrid seed product is made. Where multiple recommendations are made, the recommendations can be ranked as well as a risk assessment 189 such as shown.

FIG. 13 illustrates another embodiment of a user interface 200 that can be used in crop production applications. Site specific information is collected such as location 172, soil type 174, and number of acres 202. In addition, there is the option to import precision farming data 204 as well as import environment of frequency data 205. There are also the options to set production practices, set environmental assumptions, set risk levels, and set the maximum number of hybrids 212. Based on the inputs, a portfolio is created that includes a plurality of products 214, an associated number of acres 216 to plant for each product, a recommendation 217 of at least one hybrid seed product, a risk assessment 218, and revenue assurance 219. Where multiple recommendations are made, the recommendations can be ranked. There is also an option to generate precision farming information 220 based on this information, such as a prescription map. The present invention contemplates that the precision farming information may indicate which acres to plant with which hybrids, give specific production practice application (such as chemical application rates), or other recommendations.

Figure 14:
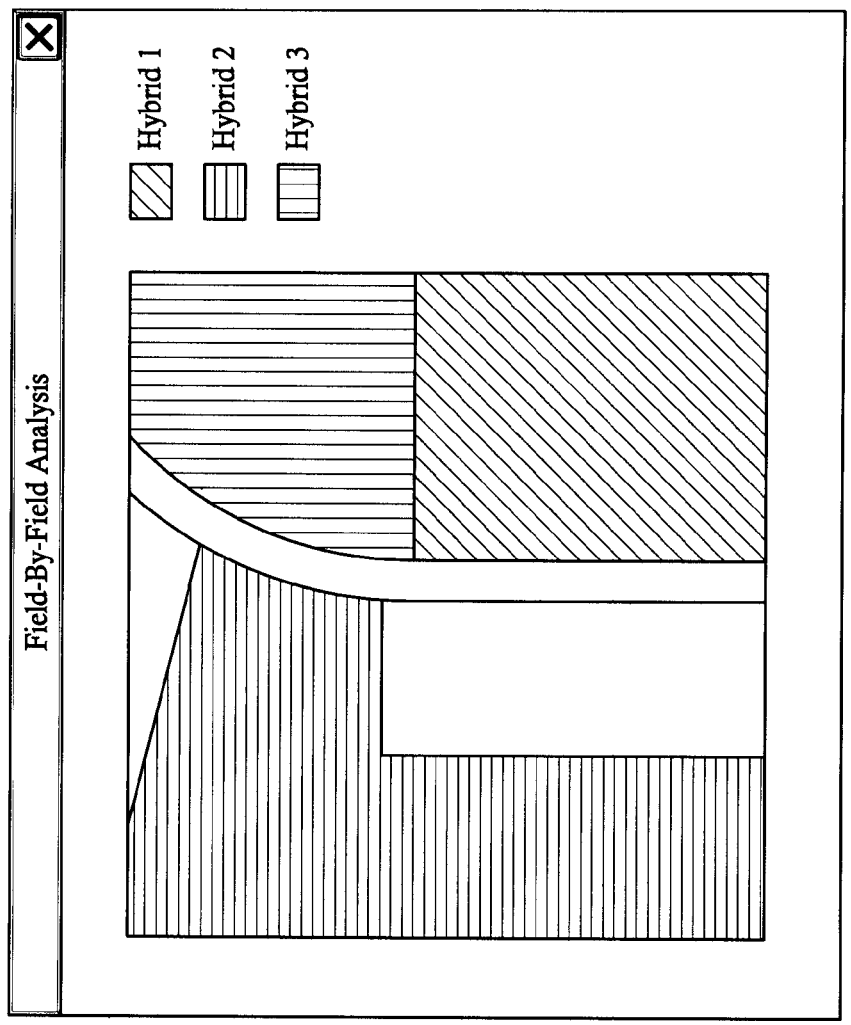
FIG. 14 is a screen display for one embodiment of the present invention showing field-by-field product recommendations.

FIG. 14 illustrates one example of a field-by-field analysis showing product recommendations for a land base of a producer. As shown in FIG. 14, different land areas within a producer's land base have different hybrids associated with them. The present invention contemplates producing such a map or field-by-field recommendations where multiple products are recommended. It should further be understood that a single producer or other user may have operations in a number of geographically diverse locations, and not necessarily the nearby fields illustrated in FIG. 14.

It should also be appreciated that the use of environmental classification and G x E interactions should be effectively communicated to customers. The effectiveness of the environmental classification process is based in part on its ability to use historical data from many locations so that all available data is used. This aspect of environmental classification would seem counter-intuitive to a customer who primarily relies upon personal knowledge in the local area. The customer's confidence in firsthand production knowledge can be used to assist in increasing confidence in environmental classification.

Figure 15:
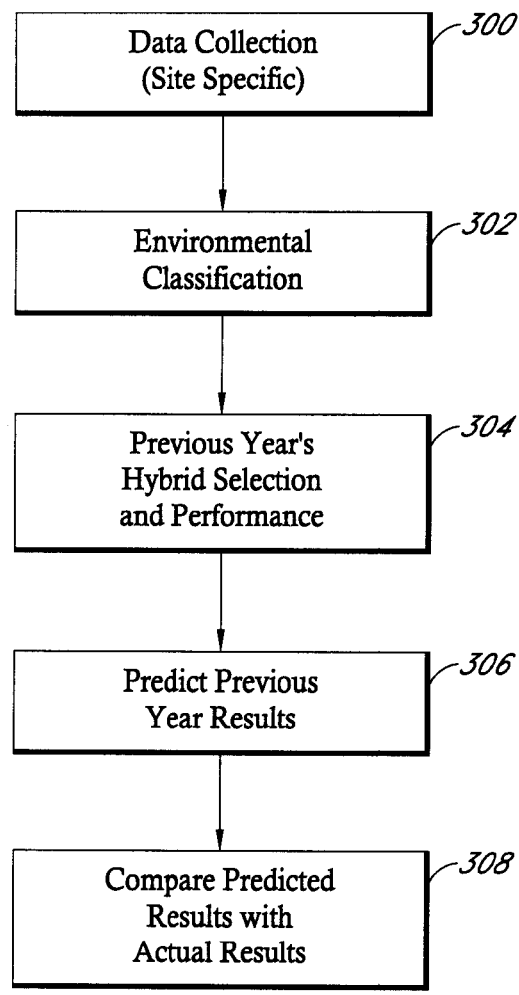
FIG. 15 is a flow diagram for one embodiment of a sales tool for demonstrating the value of environmental classification in describing relative performance.

FIG. 15 illustrates one example of the methodology of this aspect of the invention to assist in explaining these concepts to a producer. In step 300 site-specific data collection for a land base is performed. Based on this site-specific data collection, in step 302, the land base is given an environmental classification. In addition to this information, the type of hybrid selected in the previous year and its performance is provided by the producer in step 304. In step 306, a prediction is made as to the previous year's production based on environmental classification. In step 308, the predicted results are compared with the actual results. The present invention also contemplates not requiring performance results from the producer until after the previous year's results have been predicted in case the producer is not confident that an independent prediction is made.

Figure 16:
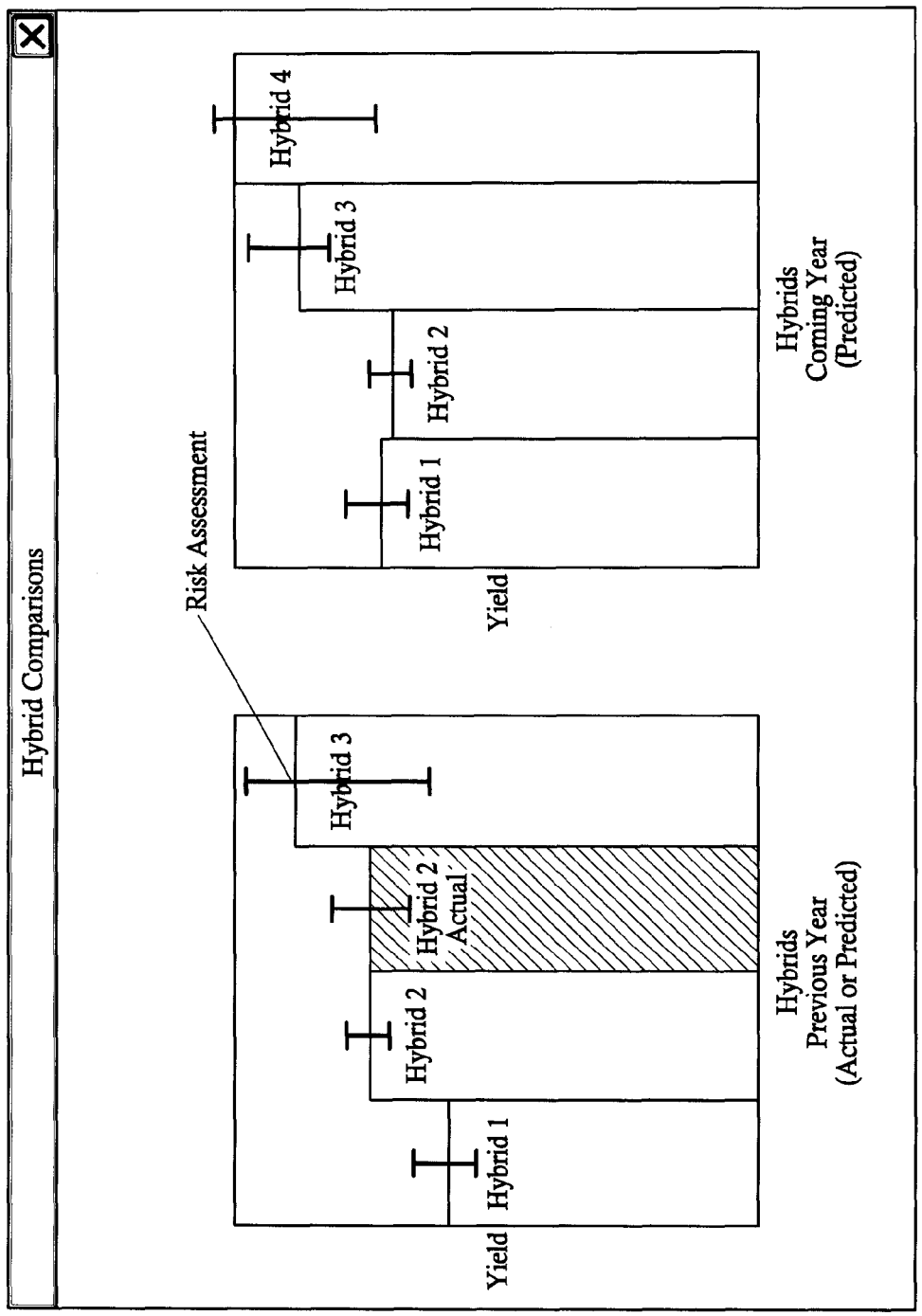
FIG. 16 is a screen display illustrating one example of output from a sales tool of the present invention for demonstrating the value of environmental classification in describing relative performance.

FIG. 16 illustrates one example of a screen display showing such comparisons. In FIG. 16, performance predictions (yield) are made for a number of different hybrids for both the previous year and the current year. In addition, a risk assessment for each hybrid may also be provided. The producer can compare the prediction for the previous year with the actual performance for that year in order to understand how well the environmental classification method can predict a result. If the producer is confident in the method's ability to correctly predict a result, the producer will be more inclined to use the prediction made for the coming year. The present invention contemplates that the same or similar information can be presented in any number of ways. It should further be understood that such a demonstrate assists in illustrating the accuracy of the system in predicting relative performance differences between seed products. Due to the number of potential variables and difficulty in controlling such variable accurate prediction of absolute performance is generally not a reasonable goal. However by selecting appropriate environmental classifications, useful insight into relative performance can be provided.

Figure 17:
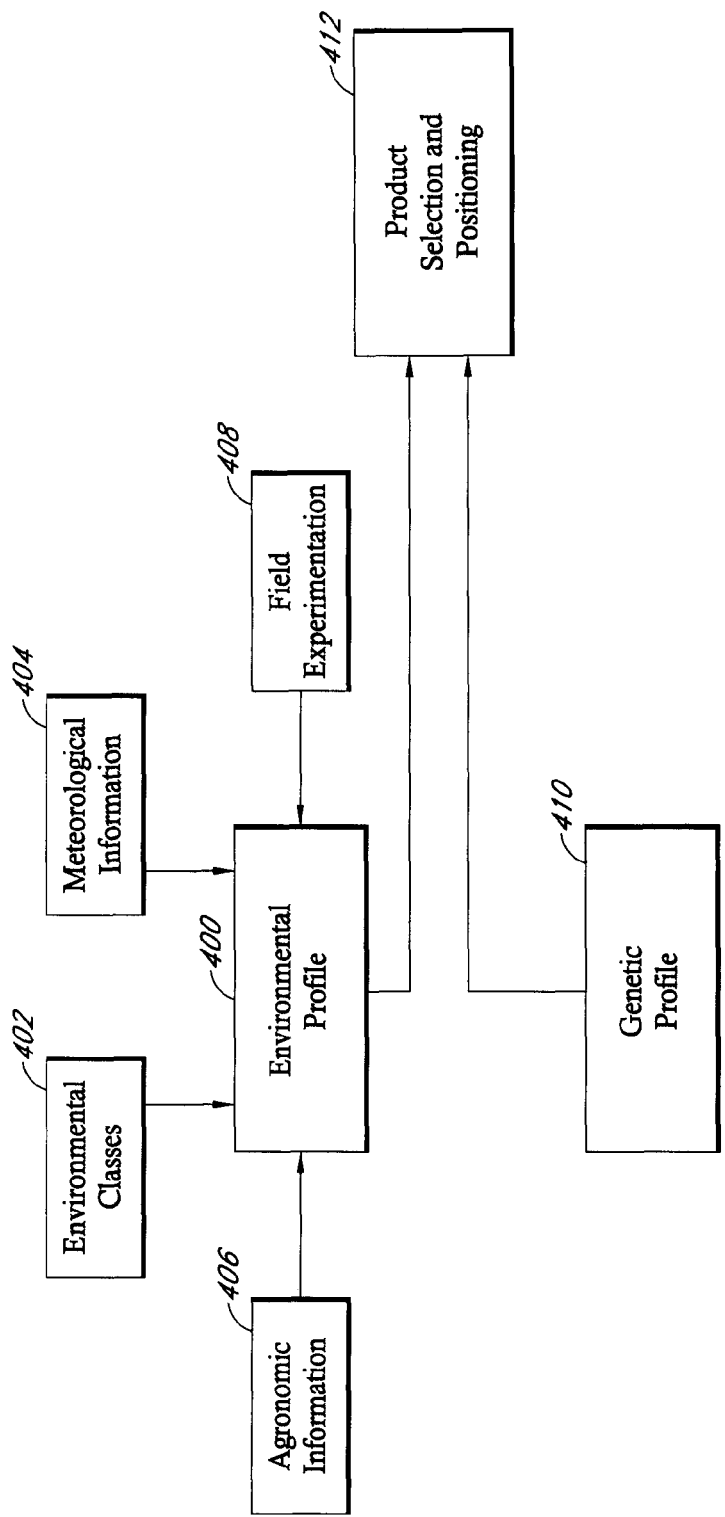
FIG. 17 is a flow diagram showing information flow in a product selection and positioning application of the present invention.

FIG. 17 provides an information flow diagram according to one embodiment of the present invention. As shown in FIG. 17, an environmental profile 400 is created which can take into consideration environmental classes 402, meteorological information 404, agronomic information 406, field experiment information 408, and other information. This information, particularly when combined with genetic profile 410 information is used to assist in product selection and positioning 412. It should be apparent that being able to directly incorporate genetic profile information 410 in making these decisions is particularly helpful. A seed company having the genetic profile information 410 will be able to use that information the first year a product is commercialized. Typically newer products have improved genetic traits or features. Yet sometimes producers are reluctant to use newer products which the producer does not have firsthand experience with. The systematic approach of the present invention allows recommendations for products to be made even in the first year a product is commercially available because past experience, such as that used in the environmental profile 400 is used. It is believed that once a producer recognizes the ability of the present invention to describe relative performance, the producer will be more willing to use the present invention even to select products which the producer not have firsthand knowledge about.

Figure 18:
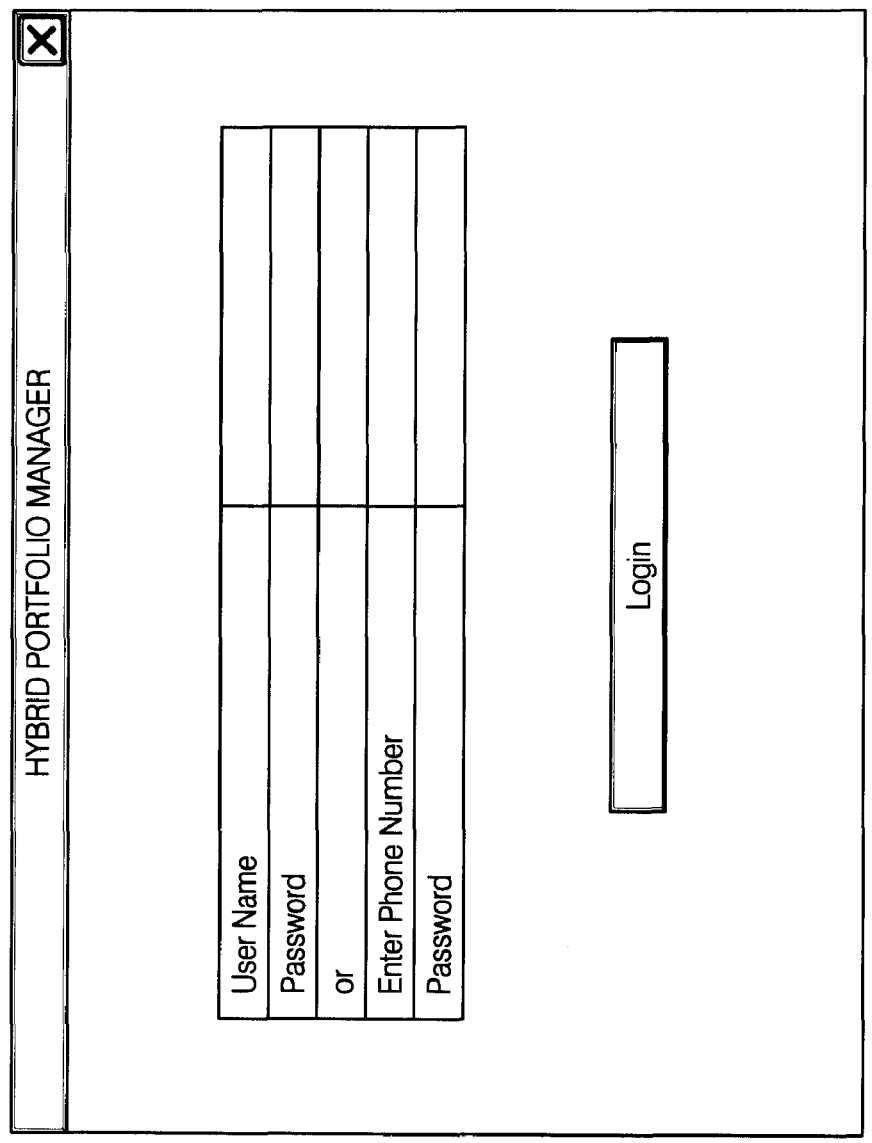
FIG. 18 illustrates a log-in screen display from one embodiment of a software tool of the present invention.
Figure 19:
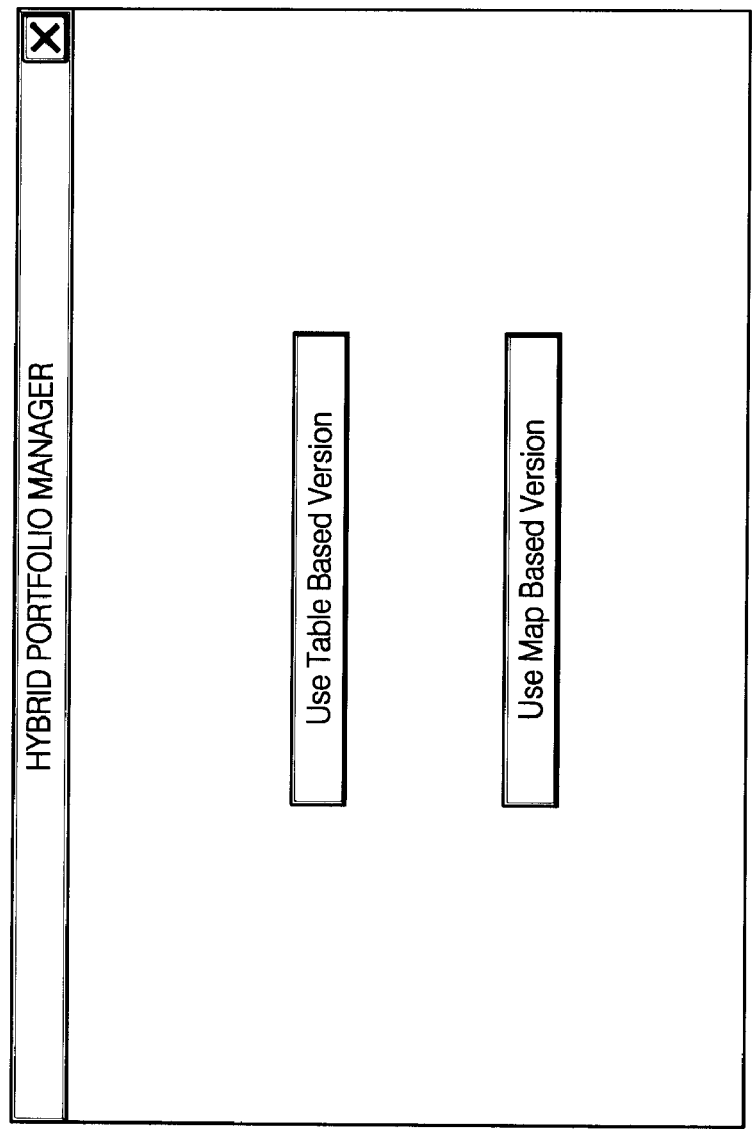
FIG. 19 is a screen display according to one embodiment of the present invention allowing a user to select whether they wish to use a table based version of the software tool or a map-based version of the software tool.
Figure 20:
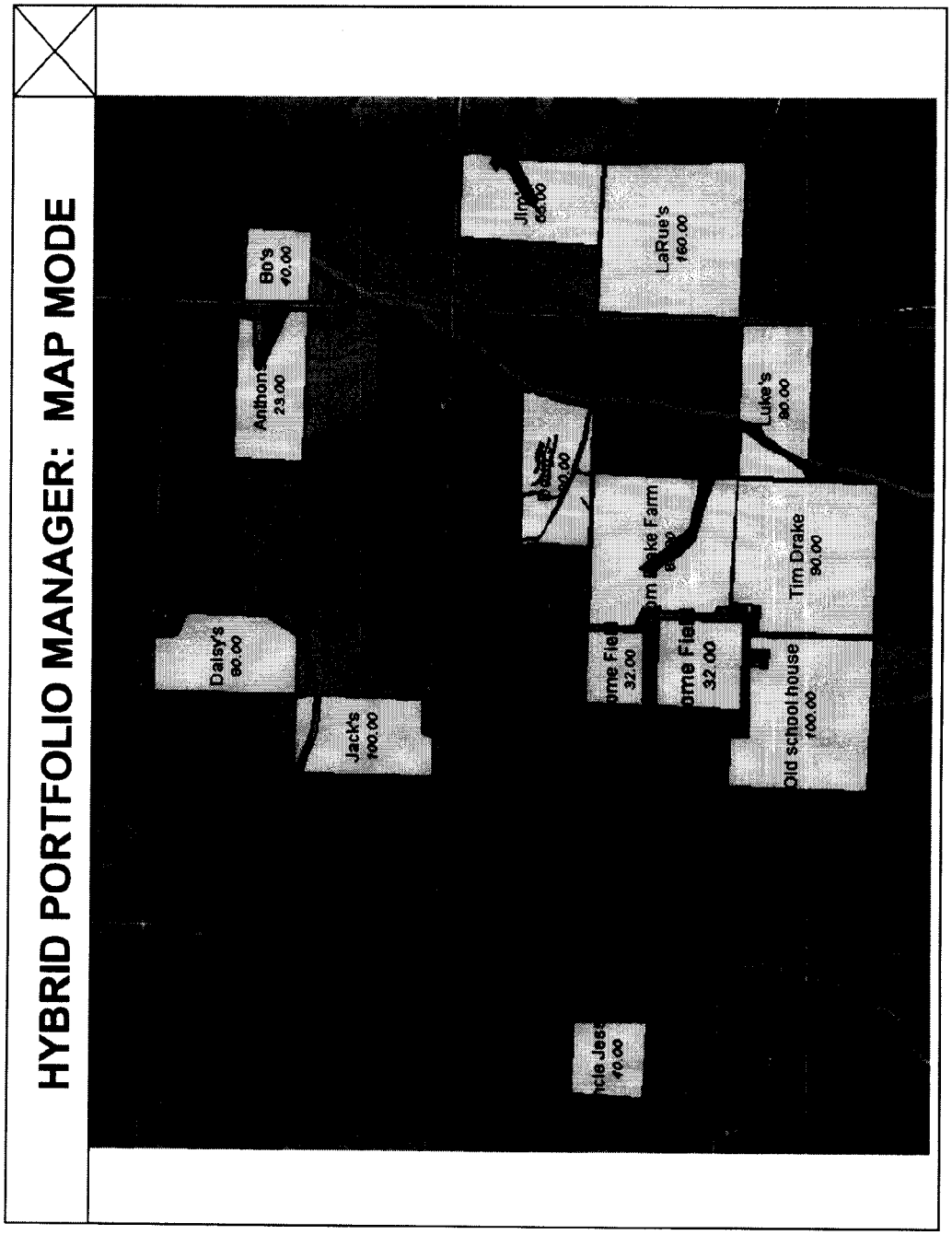
FIG. 20 is a screen display of a map-based mode of a software tool according to one embodiment of the present invention.

FIG. 18 illustrates a log-in screen display from one embodiment of a software tool of the present invention. As shown in FIG. 18, one can log-in to the software through use of their username and password or phone number and password. Upon a successful log-in, the screen display of FIG. 19 is shown. FIG. 19 allows a user to select whether they wish to use a table based version of the software tool or a map-based version of the software tool. If a user selects to use the map-based version of the software tool, then a screen display such as shown in FIG. 20 is provided. The map display illustrates a number of different fields. Note that there are field names associated with each of these fields. In addition there are field sizes, preferably in acres, associated with each of these fields. The map display of FIG. 20 thus can be used to show different fields controlled by the same producer. Knowledge of such an association is useful in making recommendations to the producer which manage risk.

Figure 21:
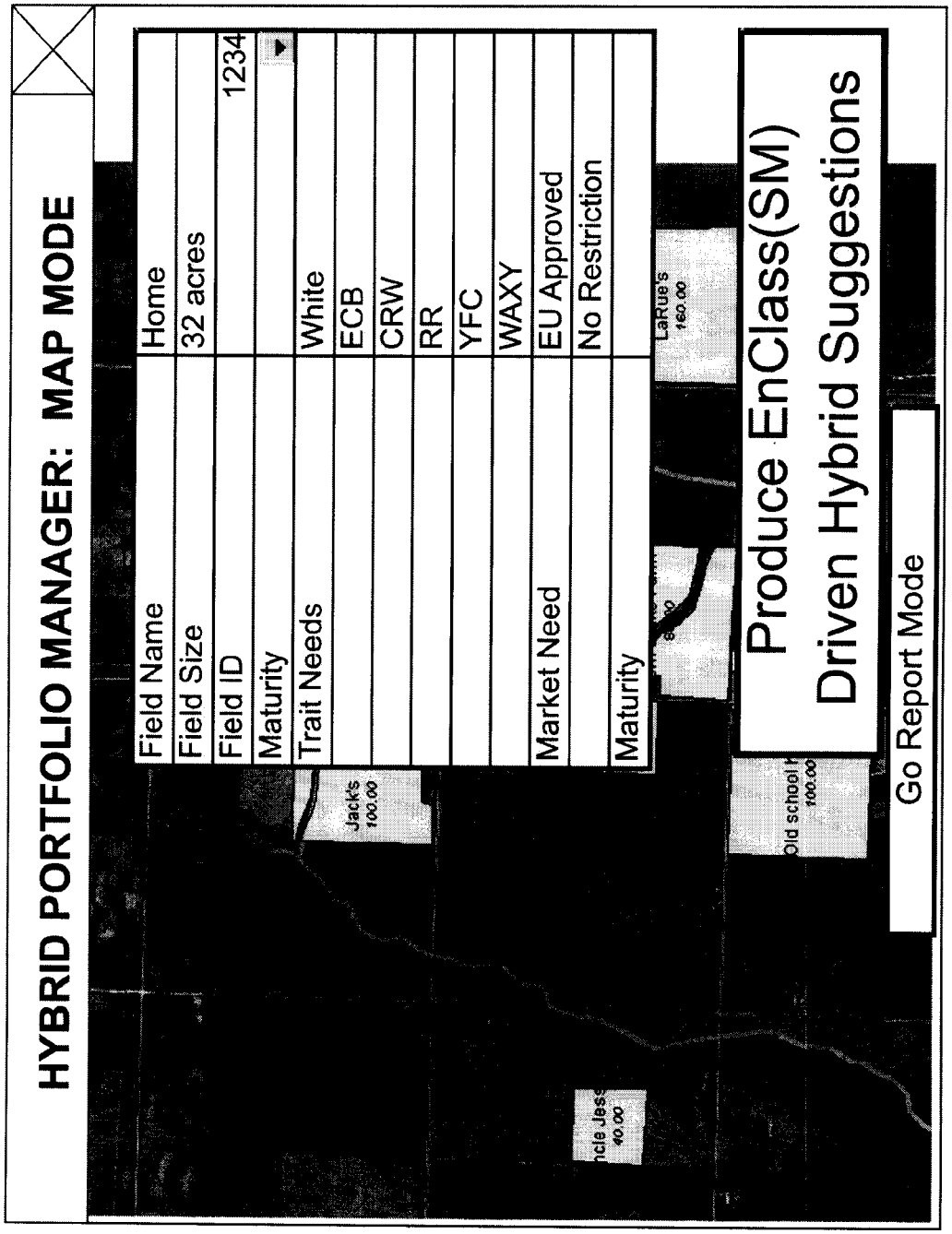
FIG. 21 illustrates one embodiment of a display that appears when one of the fields is selected.

FIG. 21 illustrates one embodiment of a display that appears when one of the fields is selected. As shown in FIG. 21, when the "Home Field" is selected, information about this field is displayed. Information which can be displayed may include the field name, the field size, a field identifier, maturity information, trait needs, market needs, and maturity. Of course, other information may also be displayed instead of or in addition to any of the shown information. A button is provided for producing hybrid suggestions using environmental classifications. In addition, button is provided for accessing the functionality associated with a reporting mode.

Figure 22:
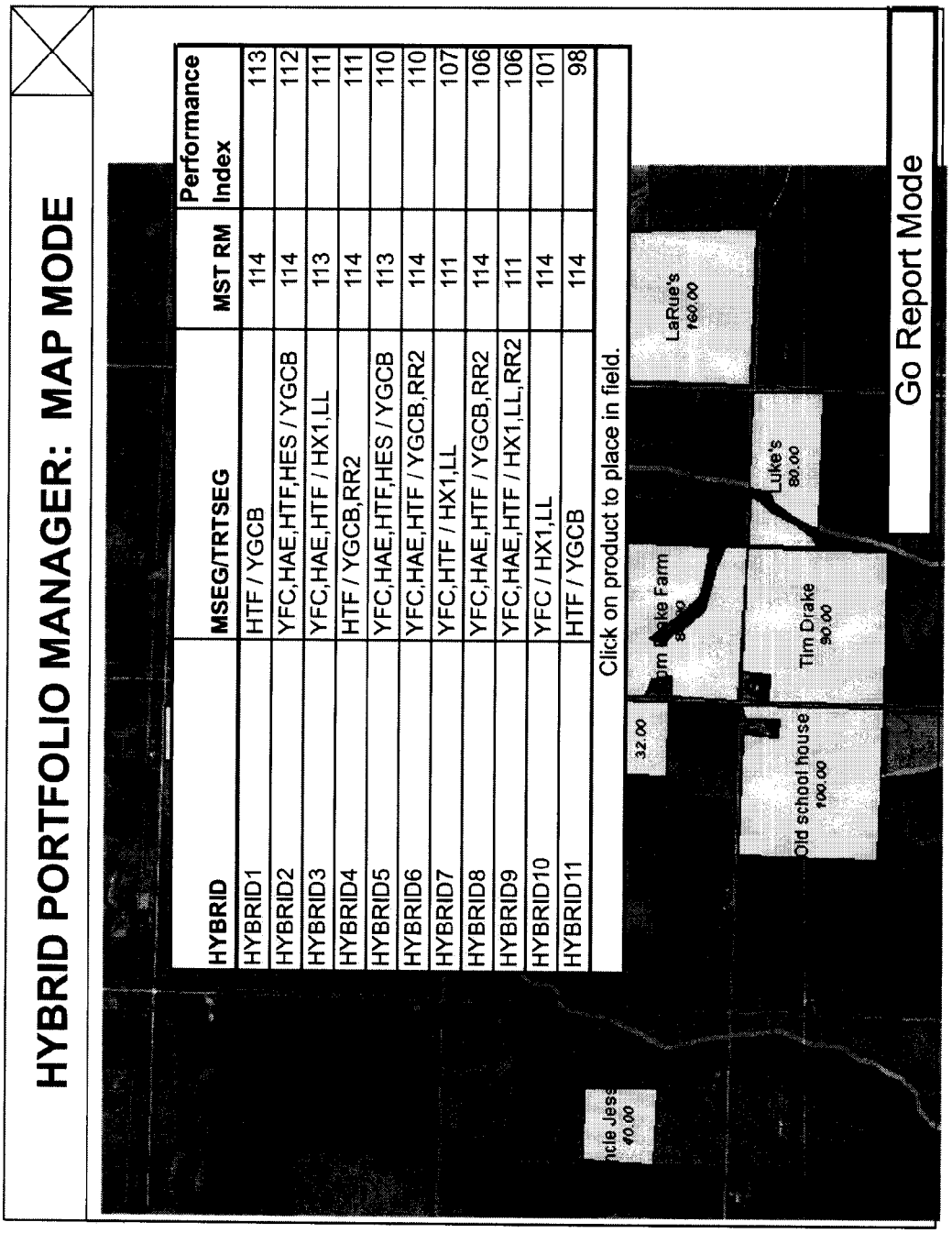
FIG. 22 shows a listing of different available seed products, marketing segments associated with each seed product, and traits associated with each seed products.
Figure 23:
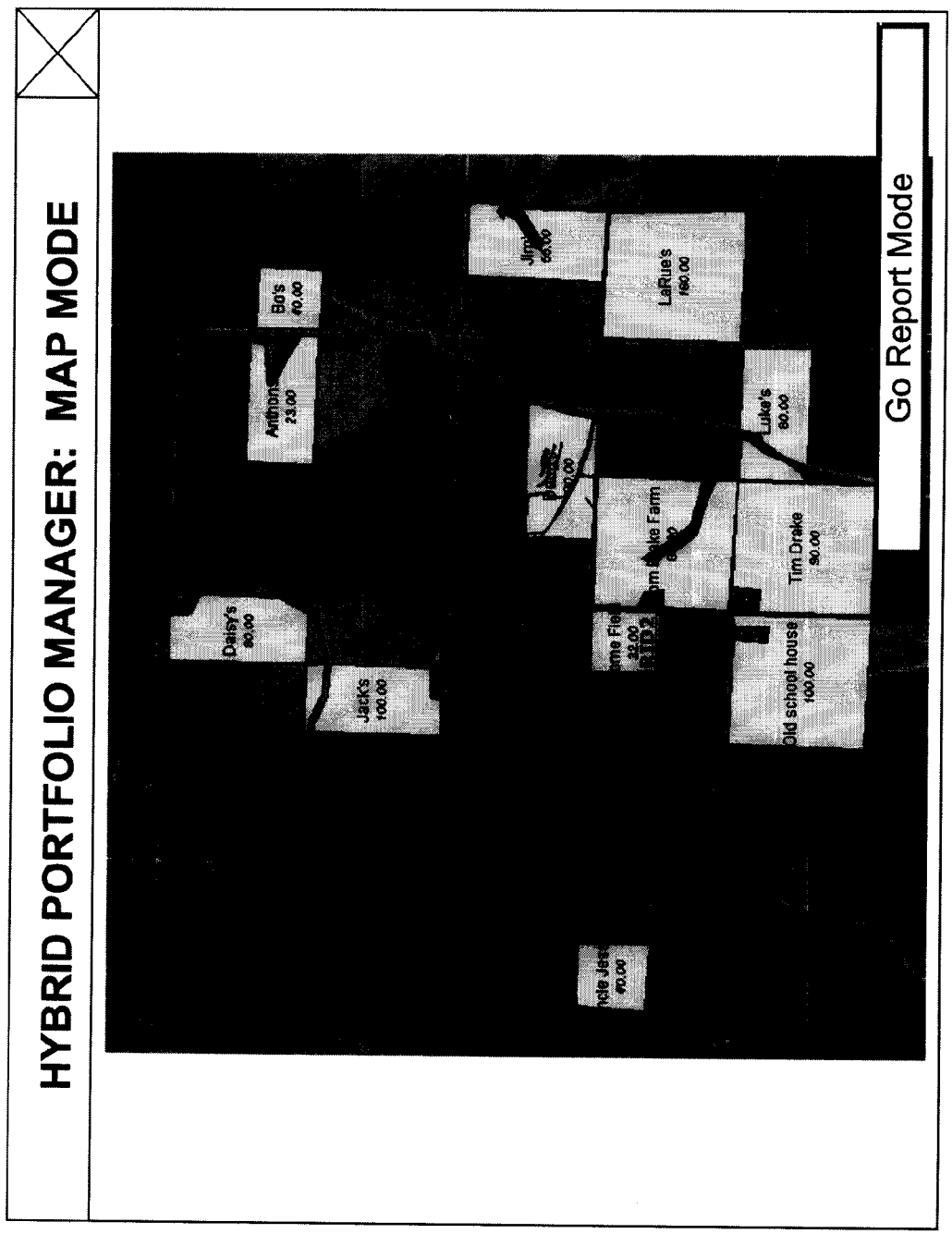
FIG. 23 illustrates a map where the name of a seed product is placed on an associated field.

FIG. 22 shows a listing of different available seed products, marketing segments associated with each seed product, and traits associated with each seed production. In addition, other information such as relative maturity and/or a performance index can be provided for each seed product. The software tool allows a seed product to be placed in each field through selecting associating the selection of a seed product with the selection of a field. FIG. 23 illustrates a map where the name of a seed product is placed on an associated field. In this case, "HYRBID2" is placed on the "Home Field." FIG. 24 provides one embodiment of a screen display in a table mode. In the table mode, each field has a name, size information, an identifier, maturity information, trait needs, and market needs. Based on this and/or other information, a recommendation can be provided for the type of seed product to plant within the field.

Figure 25:
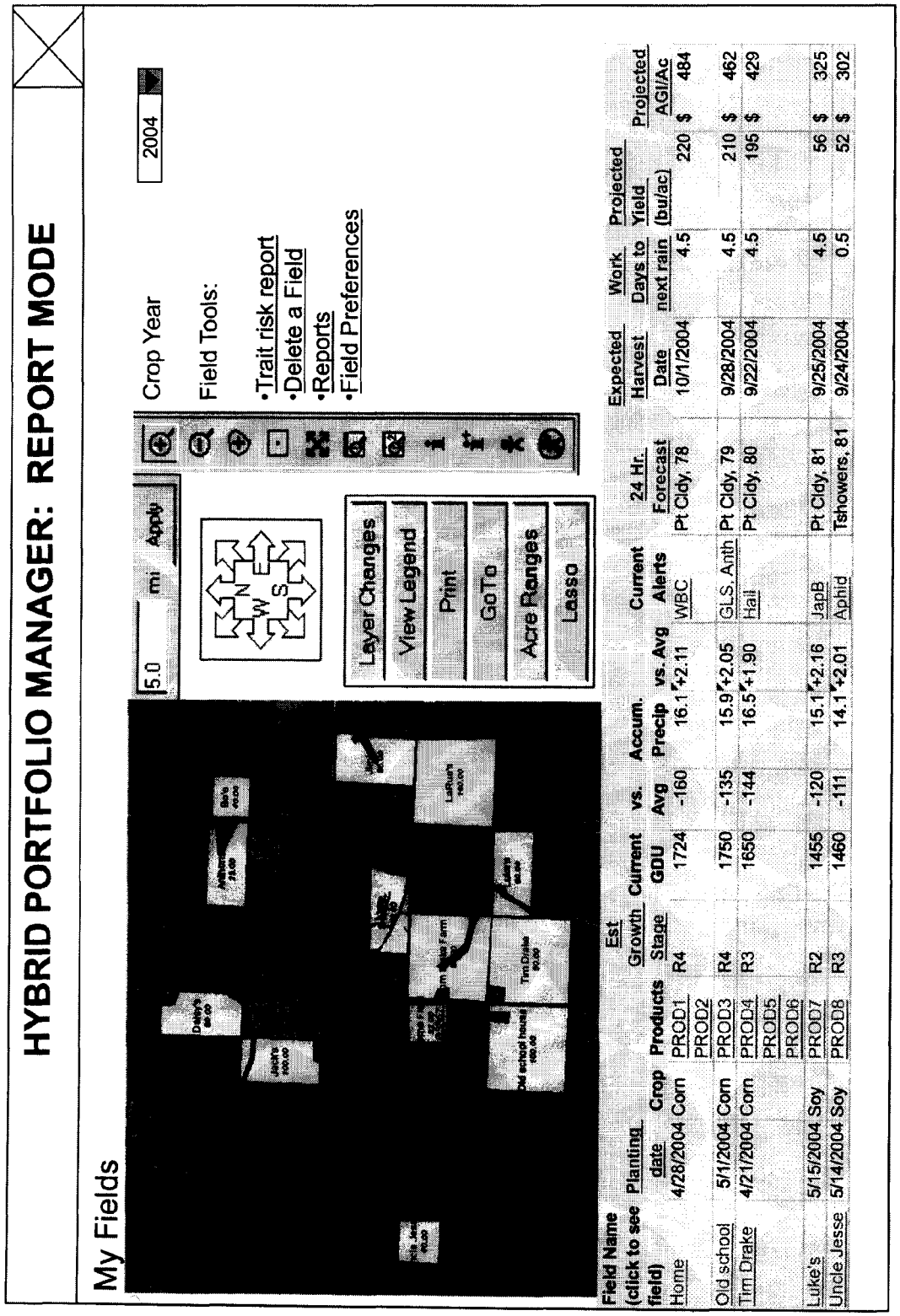
FIG. 25 provides a screen display of a report according to one embodiment of the present invention.

FIG. 25 provides a screen display of a report according to one embodiment of the present invention. In the report mode, information about different fields associated with a producer is provided. This information can include a map showing where different fields are located and their sizes. In addition controls for navigating the map be provided as well as any number of other geographic information systems (GIS) functions such as different layers, different means of selection, and other functions. The screen display of FIG. 25 also allows information about each field and the product or products associated with that field to be display. For example, for each field, one or more seed products may be listed for that field. In addition, other information about the field may be provided, including alerts for different insect or disease conditions, expected harvest days, work days to the next rain, weather forecasts, projected yield, and projected adjusted gross income per acre. The present invention contemplates that other types of information may also be displayed. Note that as shown in FIG. 25, different types of crops may be reported on, in this case both corn and soybeans.

FIG. 26 illustrates another example of a screen display associated with a reporting mode. As shown in FIG. 26, a number of different seed products, in this case hybrids, are shown along with the total number of acres planted or to be planted. In addition, a number of different attributes or traits associated with each of these seed products and scored for each of these seed products. The use of this scoring provides a producer with some understanding of which traits a particular product is likely to exhibit more strongly and which traits a product is likely to exhibit less strongly under the same or similar environmental conditions. Based on the portfolio of seed products selected, and the number of acres for each product, a weighted score is arrived upon for each product trait.

FIG. 27 illustrates another embodiment of a screen display according to one embodiment of the present invention. The screen display of FIG. 27 is a reporting tool which illustrates different seed products, the percentage of a total mix, the seed product's performance index under possible environment classes, and the frequency of particular environment classes where the seed product is planted. Using this information, a producer is provided assistance in managing risk. In the instance shown, the customer is more risk tolerant than some and is willing to accept more year to year variability in order to capitalize on high yield conditions. Thus, the producer has selected to plant the majority of acres with Hybrid X which is likely to perform better under most environment classes.

Once a producer has determined their desired product mix, the present invention provides for producing an invoice for the selected products. FIG. 28 provides a screen display according to one embodiment of the present invention. In FIG. 28, a listing of seed products is provided along with the number of acres planted, the percentage of total acres planted with that particular seed product, and the total number of units (such as bags of seed) needed. This information may be electronically transmitted to an invoicing system to thereby provide this information in the most expedited fashion to assist the seed producer in demand planning, inventory management, or otherwise and to assure that accurate and complete order information is received from the producer.

The present invention contemplates numerous variations from the specific embodiments provided herein. These include variations in the environmental classifications, performance characteristics, software or hardware where used, the type of and other variations.

All publications, patents and patent applications mentioned in the specification are indicative of the level of those skilled in the art to which this invention pertains. All such publications, patents and patent applications are incorporated by reference herein for the purpose cited to the same extent as if each was specifically and individually indicated to be incorporated by reference herein.

What is claimed:

1. A method of identifying seed products for planting by a crop producer associated with a land base, each of the seed products having a genotype, the method comprising:
    providing an environmental profile for the land base and storing information related to the environmental profile on a computer readable storage medium;
    providing a producer profile for the crop producer, including risk tolerance information,
    wherein the risk tolerance information comprises information associated with a variable amount of risk the crop producer is willing to take for at least one seed product;
    determining a recommendation of at least one seed product to plant within the land base based on the environmental profile, the producer profile, and performance of the genotype of each of the seed products in the environmental profile of the land base using a central processing unit of a computer that can access the computer readable storage medium;
    creating an output comprising identification of the at least one seed product to plant within the land base.

2. The method of claim 1 wherein the environmental profile includes an environmental classification associated with the land base.

3. The method of claim 1 wherein the step of determining the recommendation is based at least partially on genotype-by-environment interactions.

4. The method of claim 1 wherein the step of determining the recommendation is based at least partially on genotype-by-environment-by-management interactions.

5. The method of claim 1 wherein the environmental profile includes agronomic information.

6. The method of claim 1 wherein the environmental profile includes meteorological information.

7. The method of claim 1 wherein the environmental profile includes field experimentation information.

8. The method of claim 1 wherein the producer profile includes business goals of the crop producer.

9. The method of claim 1 wherein the producer profile includes productivity goals of the crop producer.

10. The method of claim 1 wherein the producer profile includes at least one item from the set consisting of no till information, size of farm information, number of farms information, landlord preference information, equipment limitations, and work force limitations.

11. The method of claim 1 wherein at least one seed product is a plurality of seed products.

12. The method of claim 1 wherein the environmental profile includes data selected from the set consisting of wind data, temperature data, solar radiation data, precipitation data, soil type data, soil pH data, planting and harvesting dates, irrigation data, tiled area data, previous crop data, fertilizer data, nitrogen level data, phosphorous level data, potassium level data, insecticide data, herbicide data, and biotic data.

13. The method of claim 1 wherein the screen display is on a computer monitor.

14. The method of claim 1 further comprising supplying the at least one seed product to the crop producer.

15. The method of claim 1 further comprising planting at least one of the seed product.

16. The method of claim 1 further comprising wherein the output further comprises at least one management recommendation.

17. The method of claim 1 wherein the performance of the genotype of each of the seed products in the environmental profile of the land base being determined by performance of the seed products in the environmental profile of the land base and by performance of genetically related seed products in the environmental profile of the land base, the genetically related seed products being genetically related to one or more of the seed products.

18. The method of claim 1 wherein one or more of the seed products having never been planted by the crop producer.

19. A method of providing seed products for planting by a crop producer associated with a land base, each of the seed products having a genotype, the method comprising:
providing a characterization of the land base and storing information related to the characterization on a computer readable storage medium;
associating acceptable risk level with the crop producer, wherein the risk level comprises information associated with a variable amount of risk the crop producer is willing to take for at least one seed product;
determining at least one seed product to plant within the land base based on the risk level, the characterization of the land base, and genotype-by-environment interactions associated with the seed products;
providing an output comprising identification of the at least one seed product to plant within the land base using a central processing unit of a computer that can access the computer readable storage medium; and
providing seeds matching the identification of the at least one seed product to the crop producer for planting on the land base.

20. The method of claim 19, wherein the characterization of the land base is based partially on environmental and/or physiological landmark data.

21. The method of claim 19 wherein the genotype-by-environment (G×E) interactions are determined at least partially based on performance data associated with the seed products.

22. The method of claim 21 wherein G×E interactions are determined by statistical methods.

23. The method of claim 21 wherein the genotype-by-environment interactions are determined at least partially based on environmental classifications associated with performance data of the seed products.

24. The method of claim 23, wherein said performance data includes at least one item from the set consisting of yield, drought resistance, grain moisture, lodging, stand establishment, emergence, midsilk, test weight, protein, oil, and starch percentage, relative maturity, plant height, seed size, disease resistance genes, heading date, resistance to insects, brittle snap, stalk breakage, resistance to fungus, seed moisture, head shape, hullability, seedling vigor, beginning bloom date, maturity date, seed shatter, winter survival, fiber strength, and color grade.

25. The method of claim 19 wherein the step of determining at least one seed product to plant within the land base is further based on genotype by environment by management interactions.

26. The method of claim 19 wherein the characterization of the land base includes an environmental characterization of the land base.

27. The method of claim 26 wherein the environmental characterization includes determining an environmental classification selected from a set of environmental classes, the set of environmental classes comprising a temperate class, a temperate dry class, a temperate humid class, a high latitude class, and a subtropical class.

28. The method of claim 26 wherein the environmental characterization includes determining an environmental classification selected from a set of environmental classes, the set of environmental classes comprising biotic classifications.

29. The method of claim 19 wherein the at least one seed product to plant is a plurality of seed products.

30. The method of claim 19 wherein the output is a printed output.

31. The method of claim 19 wherein the output is displayed on a display.

32. The method of claim 19 further comprising recommending at least one seed product to plant within the land base.

33. A method of selecting seed products for planting by a crop producer associated with a land base, each of the seed products having a genotype, the method comprising:
classifying the land base with an environmental classification and storing an indication of the environmental classification on a computer readable storage medium;
assigning a risk tolerance level to the crop producer, wherein the risk tolerance level comprises information associated with a variable amount of risk the crop producer is willing to take for at least one seed product;
determining at least one seed product to plant within the land base based on the environmental classification, the risk tolerance level, and the genotype by environment interactions associated with the seed products using a central processing unit of a computer that can access the computer readable storage medium;
providing an output comprising identification of the at least one seed product to plant within the land base.

34. The method of claim 33 wherein the output further comprises predicted performance data for the at least one seed product.

35. The method of claim 34 further comprising comparing the predicted performance data to actual data.

36. A method of determining a seed product that is likely to be a high performer for a producer's particular land base, each seed product having a genotype, the method comprising:
providing an electronic data bank comprising at least one seed product's prior performance, wherein each seed product's prior performance was determined at different locations under different environmental, biotic or abiotic conditions or a combination of said conditions;
providing a characterization of a producer's particular land base;
assigning a risk acceptance level to the producer, wherein the risk acceptance level comprises information associated with a variable amount of risk the producer is willing to take for at least one seed product;

selecting and retrieving from the electronic data bank performance data for seed products that have been grown in locations the same or similar to the producer's particular land base;

comparing with a computer processor that can access the electronic data bank the performance data of said products grown in locations similar to the producer's particular land base with one another;

determining whether a seed product performed better than other seed products;

providing an output comprising an identification of at least one seed product that is likely to be a high performer for the producer's particular land base and that is consistent with the risk acceptance level of the producer.

37. The method of claim 36 further comprising collecting data that measures at least one seed product's performance at different locations under different environmental, biotic or abiotic conditions or a combination of these conditions.

38. The method of claim 37 wherein said collected data is entered into a database.

39. The method of claim 36 wherein the characterization of the land base is based partially on environmental and/or physiological landmark data.

40. The method of claim 36 further comprising classifying the land base with an environmental classification.

41. The method of claim 40 wherein the environmental characterization includes determining an environmental classification selected from a set of environmental classes, the set of environmental classes comprising a temperate class, a temperate dry class, a temperate humid class, a high latitude class, and a subtropical class.

42. The method of claim 40 wherein the environmental characterization includes determining an environmental classification selected from a set of environmental classes, the set of environmental classes comprising biotic classifications.

43. The method of claim 40 further comprising determining environmental classification frequencies of the land base.

44. The method of claim 38 further comprising classifying seed product performance data by environmental classification.

45. The method of claim 44 further comprising weighting the data based on long-term frequencies.

46. The method of claim 39 wherein at least one seed product is selected as a high performer.

47. The method of claim 38 wherein the output is a printed output.

48. A method of selecting a portfolio of seed products for planting within a land base associated with a producer, each of the seed products having a genotype, the method comprising:
 dividing the land base into regions;
 providing an environmental profile for each of the regions of the land base to a computer;
 providing a risk tolerance level of the producer to the computer, wherein the risk tolerance level comprises information associated with a variable amount of risk the producer is willing to take for at least one seed product;
 using a processor within the computer to determine a recommendation of a plurality of seed products to plant within each region of the land base wherein the recommendation is partially based on interaction of the genotype of each seed product with the environmental profile, and relative performance of the seed product within the environmental profile across potential variations and on the risk tolerance level of the producer; and
 displaying the recommendation on a display of the computer.

49. A method of supplying a portfolio of seed products for planting within a land base associated with a producer, each of the seed products having a genotype, the method comprising:
 dividing the land base into regions;
 associating an acceptable risk level with the producer, wherein the acceptable risk level comprises information associated with a variable amount of risk the producer is willing to take for at least one seed product;
 accessing an environmental profile for each of the regions of the land base using a computer;
 determining potential variations in the environmental profile during a growing season;
 using the computer to make a recommendation for the portfolio of seed products to plant within the land base, the recommendation including a selection of at least one seed product for each region of the land base, the recommendation for the portfolio based on the environmental profile for each of the regions and potential variations in the environmental profile to thereby manage risks associated with the potential variations and based upon the acceptable risk level associated with the producer; and
 providing seeds that match the recommendation at the land base for planting.

50. The method of claim 49 wherein the risks associated with the potential variations are risks in performance.

51. The method of claim 49 wherein the risks associated with the potential variations comprise risks associated with weather conditions.

52. The method of claim 49 wherein the risks associated with the potential variations comprise risks associated with plant diseases.

53. A method of selecting a portfolio of seed products for planting within a land base controlled by a producer, the land base comprising a plurality of fields, the method comprising:
 determining a location of each of the plurality of fields controlled by the producer and a size for each of the plurality of fields;
 providing a visual depiction of the fields on a display screen showing the relative location of each of the fields within the land base;
 determining a recommendation of a plurality of seed products to plant within each field, wherein the recommendation being at least partially based on performance of the plurality of seed products under a range of environmental classifications and upon a risk tolerance level of the producer to thereby manage overall production risk for the producer, wherein the risk tolerance level comprises information associated with a variable amount of risk the producer is willing to take for at least one seed product;
 displaying the recommendation on the display screen.

54. The method of claim 53 further comprising receiving from the producer confirmation of a mix of seed products to plant.

55. The method of claim 54 further comprising receiving information for invoicing from the producer.

56. An article of software stored on a computer readable medium and adapted for assisting a producer in selecting a mix of seed products to plant within a land base comprising a plurality of fields controlled by the producer, the software comprising:
 instructions on the computer readable medium for providing a first screen display adapted for identifying the plurality of fields controlled by the producer and a size of each of the plurality of fields;

instructions on the computer readable medium for associating a risk tolerance level with the producer, wherein the risk tolerance level comprises information associated with a variable amount of risk the producer is willing to take for at least one seed product;

instructions on the computer readable medium for providing a second screen display adapted for displaying performance of a plurality of seed products over a range of environment classes;

instructions on the computer readable medium for providing a reporting mode adapted for reporting which one or more of the plurality of seed products to plant within each of the plurality of fields based at least in part on the risk tolerance level associated with the producer.

57. The article of software of claim 56 further comprising means to electronically communicate information to an invoicing system.

58. A method of planting seed products by a crop producer associated with a land base, each of the seed products having a genotype, the method comprising: associating a risk tolerance level with the crop producer;

characterizing the land base by selecting an environmental profile for the land base from a set of a plurality of environmental profiles;

determining a recommendation of at least one seed product to plant within the land base based on the environmental profile, the risk tolerance level associated with the crop producer, and performance of the genotype of each of the seed products in the environmental profile, wherein the risk tolerance level comprises information associated with a variable amount of risk the crop producer is willing to take for at least one seed product, and wherein the recommendation being formed without data for performance of each of the seed products within the land base;

providing an output comprising identification of the at least one seed product to plant within the land base;

obtaining seeds that match the identification; and planting the obtained seeds on the land base.

* * * * *